United States Patent
Isgum et al.

(10) Patent No.: US 12,089,977 B2
(45) Date of Patent: Sep. 17, 2024

(54) METHOD AND SYSTEM FOR ASSESSING VESSEL OBSTRUCTION BASED ON MACHINE LEARNING

(71) Applicant: Pie Medical Imaging B.V., Maastricht (NL)

(72) Inventors: Ivana Isgum, Nieuwegein (NL); Majd Zreik, Utrecht (NL); Tim Leiner, Utrecht (NL); Jean-Paul Aben, Limbricht (NL)

(73) Assignee: Pie Medical Imaging B.V., Maastricht (NL)

( * ) Notice: Subject to any disclaimer, the term of this patent is extended or adjusted under 35 U.S.C. 154(b) by 469 days.

(21) Appl. No.: 17/317,746

(22) Filed: May 11, 2021

(65) Prior Publication Data

US 2021/0334963 A1    Oct. 28, 2021

Related U.S. Application Data

(63) Continuation-in-part of application No. 16/508,996, filed on Jul. 11, 2019, now Pat. No. 11,004,198.
(Continued)

(51) Int. Cl.
*A61B 6/50* (2024.01)
*G06F 18/2411* (2023.01)
(Continued)

(52) U.S. Cl.
CPC .......... *A61B 6/507* (2013.01); *G06F 18/2411* (2023.01); *G06N 3/088* (2013.01);
(Continued)

(58) Field of Classification Search
CPC ............... G06T 7/0012; G06T 7/10; G06T 2207/20081; G06T 2207/30104;
(Continued)

(56) References Cited

U.S. PATENT DOCUMENTS

| 7,369,691 B2 | 5/2008 | Kondo |
| 7,379,062 B2 | 5/2008 | Poole |

(Continued)

FOREIGN PATENT DOCUMENTS

| CN | 102202562 A | 7/2012 |
| CN | 102608089 A | 7/2012 |

(Continued)

OTHER PUBLICATIONS

Recent Research on Myocardial Microcirculation and Microcirculatory Resistance Indexes, Guo Yulong et al., Chinese Journal of Interventional Cardilogy, Dec. 2013, vol. 21. No. 6.
(Continued)

*Primary Examiner* — Mark Roz
(74) *Attorney, Agent, or Firm* — Gordon & Jacobson, P.C.

(57) ABSTRACT

Methods and systems are provided for assessing the presence of functionally significant stenosis in one or more coronary arteries, further known as a severity of vessel obstruction. The methods and systems can implement a prediction phase that comprises segmenting at least a portion of a contrast enhanced volume image data set into data segments corresponding to wall regions of the target organ, and analyzing the data segments to extract features that are indicative of an amount of perfusion experiences by wall regions of the target organ. The methods and systems can obtain a feature-perfusion classification (FPC) model derived from a training set of perfused organs, classify the data segments based on the features extracted and based on the FPC model, and provide, as an output, a prediction indicative of a severity of vessel obstruction based on the classification of the features.

16 Claims, 19 Drawing Sheets

Related U.S. Application Data which is a continuation of application No. 16/241,165, filed on Jan. 7, 2019, now Pat. No. 10,395,366, which is a continuation of application No. 15/933,854, filed on Mar. 23, 2018, now Pat. No. 10,176,575.

(60) Provisional application No. 62/476,382, filed on Mar. 24, 2017.

(51) Int. Cl.
  *G06N 3/088* (2023.01)
  *G06T 7/00* (2017.01)
  *G06T 7/10* (2017.01)
  *G06V 10/44* (2022.01)
  *G06V 10/762* (2022.01)
  *G06V 10/764* (2022.01)
  *G06V 20/64* (2022.01)
  *G16H 30/40* (2018.01)
  *G16H 50/50* (2018.01)

(52) U.S. Cl.
  CPC .............. *G06T 7/0012* (2013.01); *G06T 7/10* (2017.01); *G06V 10/443* (2022.01); *G06V 10/763* (2022.01); *G06V 10/764* (2022.01); *G06V 20/653* (2022.01); *G16H 30/40* (2018.01); *G16H 50/50* (2018.01); *G06T 2207/20081* (2013.01); *G06T 2207/30104* (2013.01); *G06V 2201/03* (2022.01)

(58) Field of Classification Search
  CPC .............. G06K 9/6269; G06K 9/00214; G06K 2209/05; G06N 3/088; G16H 50/50; G16H 30/40; A61B 6/507
  USPC ........................................................ 382/128
  See application file for complete search history.

(56) References Cited

U.S. PATENT DOCUMENTS

| | | | |
|---|---|---|---|
| 7,822,254 B2 | 10/2010 | Yatziv | |
| 8,073,227 B2 | 12/2011 | Gulsun | |
| 8,315,812 B2 | 11/2012 | Taylor | |
| 8,526,699 B2 | 9/2013 | Mittal | |
| 8,538,105 B2 | 9/2013 | Masumoto | |
| 9,008,386 B2 | 4/2015 | Verstraeten | |
| 9,195,801 B1 | 11/2015 | Sankaran | |
| 9,747,525 B2 | 8/2017 | Sauer | |
| 10,176,575 B2 | 1/2019 | Isgum | |
| 10,192,352 B2 | 1/2019 | De Vaan | |
| 10,395,366 B2 | 8/2019 | Isgum | |
| 10,699,407 B2 | 6/2020 | Isgum | |
| 10,748,285 B2 | 8/2020 | Igarashi | |
| 11,004,198 B2 | 5/2021 | Isgum | |
| 11,599,996 B2 | 3/2023 | Isgum | |
| 2005/0059876 A1 | 3/2005 | Krishnan | |
| 2005/0065421 A1 | 3/2005 | Burckhardt | |
| 2005/0207630 A1 | 9/2005 | Chan | |
| 2010/0021025 A1 | 1/2010 | Hof | |
| 2010/0067760 A1 | 3/2010 | Zhang | |
| 2010/0076296 A1 | 3/2010 | Mittal | |
| 2010/0298719 A1 | 11/2010 | Kock | |
| 2011/0224542 A1 | 9/2011 | Mittal | |
| 2012/0072190 A1 | 3/2012 | Sharma | |
| 2012/0078097 A1 | 3/2012 | Wang | |
| 2012/0121151 A1 | 5/2012 | Bernhardt | |
| 2012/0134564 A1 | 5/2012 | Zheng | |
| 2012/0207365 A1 | 8/2012 | Verstraeten | |
| 2014/0073977 A1 | 3/2014 | Grady | |
| 2015/0112182 A1 | 4/2015 | Sharma | |
| 2015/0262357 A1 | 9/2015 | Igarashi | |
| 2016/0085936 A1 | 3/2016 | Sankaran | |
| 2016/0148372 A1 | 5/2016 | Itu | |
| 2017/0046616 A1 | 2/2017 | Socher | |
| 2017/0245821 A1 | 8/2017 | Itu | |
| 2017/0258433 A1 | 9/2017 | Gulsun | |
| 2017/0262733 A1 | 9/2017 | Gulsun | |
| 2018/0025255 A1 | 1/2018 | Poole | |
| 2018/0032653 A1 | 2/2018 | Aben | |
| 2018/0253531 A1 | 9/2018 | Sharma | |
| 2018/0276817 A1 | 9/2018 | Isgum | |
| 2019/0130578 A1 | 5/2019 | Gulsun | |
| 2019/0139219 A1 | 5/2019 | Isgum | |
| 2019/0318476 A1 | 10/2019 | Isgum | |
| 2019/0380593 A1 | 12/2019 | Bouwman | |

FOREIGN PATENT DOCUMENTS

| | | |
|---|---|---|
| CN | 102902978 A | 1/2013 |
| CN | 103129568 A | 6/2013 |
| JP | 2007502676 | 2/2007 |
| JP | 2008086566 | 4/2008 |
| JP | 2014532509 | 12/2014 |
| JP | 2015527901 | 9/2015 |
| JP | 2016500484 | 1/2016 |
| JP | 2016521138 | 7/2016 |
| WO | 2015058044 | 4/2015 |

OTHER PUBLICATIONS

Chinese Office Action and Supplemental Search Report dated Oct. 13, 2023 of Application No. 201880020710.7.

CN Office Action dated Mar. 24, 2023 and Search Report dated Mar. 19, 2023 of Application No. 201880020710.7.

Automatic Plaque Detection in IVOCT Pullbacks Using Convulutional Neural Networks, Nils Gessert et al., IEEE, 2018, pp. 426-434 (Year: 2018).

"The Synthesized Vectorcardiogram Resembles the Measured Vectorcardiogram in Patients with Dyssynchronous Heart Failure," Engels et al., J Electrocardiol;48(4):586-592.

"Vectorcardiogram Synthesized From a 12-Lead ECG: Superiority of the Inverse Dower Matrix," Journal of Electrocardiology, Dec. 1988, 21(4):361-7.

"Web-Scale K-Means Clustering," D. Sculley, Proceedings of the 19th international conference on World wide web, ACM, 2010, pp. 1177-1178.

International Search Report and Written Opinion dated Aug. 16, 2019 of International Application No. PCT/EP2019/059051.

International Search Report and Written Opinion dated Jul. 25, 2018 for Application No. PCT/IB2018/051985.

Limitations of Noninvasive Measurement of Fractional Flow Reserve from Coronary Computed Tomography Angiography, De Caterina et al., Journal of the American College of Cardiology, vol. 59, Issue 15, Apr. 2012.

Validation of 3-Dimensional Quantitative Coronary Angiography based software to calculate vessel-FFR (the FAST study), Masdhedu et al., EuroPCR 2018.

Assessment of Coronary Artery Disease Severity by Positron Emission Tomography, Linda L. Demer et al., 1989, pp. 825-835 ( Year: 1989).

Automatic coronary artery lumen segmentation in computed tomography angiography using paired multi-scale 3D CNN, Fei Chen et al., SPIE, 2018, pp. 1-8 (Year: 2018).

Automatic Detection and Characterization of Coronary Artery Plaque and Stenosis using a Recurrent Convolutional Neural Network in Coronary CT Angiography, Majd Zreik et al., arXiv, Apr. 12, 2018, pp. 1-13 (Year: 2018).

A machine-learning approach for computation of fractional flow reserve from coronary computed tomography, Lucian Itu et al., J of Applied Physics, 2016, pp. 42-52 (Year: 2016).

Identifying Coronary Stenosis Using an Image-Recognition Neural Network, Lucy S. Goodenday et al., IEEE, 0739.5175, 1997,pp. 139-144 (Year: 1997).

"A Recurrent CNN for Automatic Detection and Classification of Coronary Artery Plaque and Stenosis in Coronary CT Angiography", Majd Zreik et al., arxiv.org, Cornell University Library, 20182018.

"A survey on deep learning in medical image analysis", Litjens et al. Med Image Anal. Dec. 2017; 42:60-88.

(56) References Cited

OTHER PUBLICATIONS

"A Survey on Deep Learning in Medical Image Analysis", Litjens Geert et al., Medical Image Analysis, vol. 24, Jul. 26, 2017, pp. 60-88.
"A survey on the application of recurrent neural networks to statistical language modeling", Mulder et al., Computer Speech & Language, vol. 30, No. 1, pp. 61-98, 2015.
"Attention-based deep multiple instance learning", Ilse et al., Jun. 28, 2018, arXiv preprint arXiv:1802.04712.
"Auto-encoding variational bayes", Kingma et al. May 1, 2014, arXiv preprint arXiv:1312.6114, 2013.
"Batch normalization: Accelerating deep network training by reducing internal covariate shift", Ioffe et al., in Proceedings of the 32nd International Conference on Machine Learning, 2015, pp. 448-456.
'Coronary artery centerline extraction in cardiac CT angiography using a CNN-based orientation classifier', Vvolterink et al., Med Image Anal. Jan. 2019;51:46-60.
"Deep sparse rectifier neural networks", Glorot et al., International Conference on Artificial Intelligence and Statistics, 2011, pp. 315-323.
"Graph convolutional networks for coronary artery segmentation in cardiac CT angiography", Wolterink et al., International Workshop on Graph Learning in Medical Imaging. Springer, Cham, 2019.
"Long-term recurrent convolutional networks for visual recognition and description" Donahue et al., in Proceedings of the IEEE Conference on Computer Vision and Pattern Recognition, 2015, pp. 2625-2634.
"Oriented Gaussian Mixture Models for Nonrigid 2D/3D Coronary Artery Registration", Baka et al., IEEE Trans Med Imaging. May 2014; 33(5):1023-34.
"Recurrent Fully Convolutional Neural Networks for Multi-slice MRI Cardiac Segmentation", Poudel Rudra P. et al, International Conference on Computer Analysis of Images and patterns, 2017.
"Semi-automatic coronary artery centerline extraction in computed tomography angiography data", Metz et al., proceedings / IEEE International Symposium on Biomedical Imaging: from nano to macro, May 2007.
"Semi-supervised learning with deep generative models", Kingma et al., Advances in neural information processing systems, 2014, pp. 3581-3589.
"Standardized evaluation framework for evaluating coronary artery stenosis detection, stenosis quantification and lumen segmentation algorithms in computed tomography angiography", Kiris et al., Medical Image Analysis, vol. 17, No. 8, pp. 859-876,2013.
"3D Active Shape Model Matching for Left Ventricle Segmentation in Cardiac CT," Van Assen et al., Phytochemistry Jan. 2003, 5032.
"Adenosine Stress 64-and 256-Row Detector Computed Tomography Angiography and Perfusion Imaging a Pilot Study Evaluating the Transmural Extent of Perfusion Abnormalities to Predict Atherosclerosis Causing Myocardial Ischemia," George et al., Circulation: Cardiovascular Imaging 2 (3) (2009) 174-182.
"Aligning Coronary Anatomy and Myocardial Perfusion Territories: An Algorithm for the CORE320 Multicenter Study," Cerci et al., Circ Cardiovasc Imaging. 2012, 5:587-595.
"Assessment of coronary stenoses by myocardial perfusion imaging during pharmacologic coronary vasodilation. VII. Validation of coronary flow reserve as a single integrated functional measure of stenosis severity reflecting all its geometric dimensions", Kirkeeide et al., J Am Coll Cardiol. Jan. 1986;7(1):103-13.
"Automated 3-Dimensional Quantification of Noncalcified and Calcified Coronary Plaque from Coronary CT Angiography," Dey et al., Cardiovascular Computed Tomography 2009, 3(6):372-382.
"Automatic Coronary Artery Calcium Scoring in Cardiac CT Angiography Using Paired Convolutional Neural Networks," Wolterink et al., Medical Image Analysis, 2016.
"Automatic Segmentation of the Left Ventricle in Cardiac CT Angiography Using Convolutional Neural Networks," Zreik et al., 2016 IEEE 13th International Symposium on Biomedical Imaging (ISBI), 2016, pp. 40-43.
"Bringing It All Together: Integration of Physiology With Anatomy During Cardiac Catheterization," Neil S. Kleiman, MD., Journal of the American College of Cardiology, 2011; vol. 58, No. 12:1219-1221.
"Comprehensive Assessment of Coronary Artery Stenoses: Computed Tomography Coronary Angiography Versus Conventional Coronary Angiography and Correlation with Fractional Flow Reserve in Patients with Stable Angina," Meijboom et al., Journal of the American College of Cardiology, 2008; vol. 52, No. 8:636-643.
"Computational Fluid Dynamics Applied to Cardiac Computed Tomography for Noninvasive Quantification of Fractional Flow Reserve," Charles A. Taylor, PhD et al., Journal of the American College of Cardiology, vol. 61, No. 22, 2013.
"Convolutional Deep Belief Networks for Scalable Unsupervised Learning of Hierarchical Representations," Lee et al., Proceedings of the 26th Annual International Conference on Machine Learning, 2009, pp. 609-616.
"Coronary centerline extraction from CT coronary angiographic images using a minimum cost path approach," Metz et al., Med Phys. Dec. 2009;36(12):5568-79.
"Deep Learning (Adaptive Computation and Machine Learning series)," Goodfellow et al., Nov. 18, 2016, ISBN 10:0262035618.
"Fast and Accurate Deep Network Learning by Exponential Linear Units (ELUs)," Clevert et al., International Conference on Learning Representations, 2016.
"Gradient Methods for Minimizing Composite Objective Function," Nesterov et al., Tech. rep., UCL (2007).
"Graph attention networks for segment labeling in coronary artery trees", Nils Hampe et al., Proc. SPIE 11596, Medical Imaging 2021: Image Processing, 115961I (Feb. 15, 2021); doi: 10.1117/12.2581219.
"Learning Patient-Specific Lumped Models for Interactive Coronary Blood Flow Simulations", Nickisch et al., International Conference on Medical Image Computing and Computer-Assisted Intervention, Springer, 2015, pp. 433-441.
"Left Ventricular Shape Variation in Asymptomatic Populations: the Multi-Ethnic Study of Atherosclerosis," Medrano-Gracia et al., Journal of Cardiovascular Magnetic Resonance Jul. 30, 2014;16:56.
"Measurement of Fractional Flow Reserve to Assess the Functional Severity of Coronary-Artery Stenoses," Nico H.J. Pijls, MD et al., New England Journal of Medicine 1996, vol. 334, No. 26:1703-1708.
"Model Prediction of Subendocardial Perfusion of the Coronary Circulation in the Presence of an Epicardial Coronary Artery Stenosis," Med Biol Eng Comput 2008, 46:421-432.
"Myocardial Perfusion: Near-Automated Evaluation from Contrast Enhanced MR Images Obtained at Rest and During Vasodilator Stress", Tarroni, Radiology 2012 (Year 2012).
"Myocardial Strain Estimation from CT: Towards Computeraided Diagnosis on Infarction Identification," Wong et al., SPIE Medical Imaging Conference, Mar. 2015, DOI 10.1117/12.2081464.
"Patient-Specific Coronary Blood Supply Territories for Quantitative Perfusion Analysis," Zakkaroff et al., Computer Methods in Biomechanics and Biomedical Engineering: Imaging & Visualization 2016.
"Patient-Specific Mappings Between Myocardial and Coronary Anatomy," Termeer et al., Scientific Visualization: Advanced Concepts, 2010, p. 196-209.
"Patient-Specific Modeling of Blood Flow and Pressure in Human Coronary Arteries," Kim et al., Annals of Biomedical Engineering, vol. 38, No. 10, pp. 3195-3209, 2010.
"Perfusion Territories Subtended by Penetrating Coronary Arteries Increase in Size and Decrease in Number Toward the Subendocardium," Am J Physiol Heart Circ Physiol 2014, 306: H496-H504.
"Physiologic basis for assessing critical coronary stenosis. Instantaneous flow response and regional distribution during coronary hyperemia as measures of coronary flow reserve", Gould et al., Am J Cardiol. Jan. 1974;33(1):87-94.
"Principal Component Analysis Used to Derive Patient-Specific Load-Free Geometry and Estimate Myocardial Stiffness in the Heart," Wang et al., 5th International Conference on Computational and Mathematical Biomedical Engineering—CMBE2017.

(56) References Cited

OTHER PUBLICATIONS

"Representation Learning: A Review and New Perspectives," Bengio et al., IEEE Trans. Pattern Anal. Mach. Intell. 35(8), 2013, 1798-1828.

"SCCT Guidelines for the Performance and Acquisition of Coronary Computed Tomographic Angiography: A Report of the Society of Cardiovascular Computed Tomography Guidelines Committee Endorsed by the North American Society for Cardiovascular Imaging (NASCI)," Abbara et al., Journal of Cardiovascular Computed Tomography, Nov.-Dec. 2016;10(6):435-449.

"Segmentation of the Left and Right Cardiac Ventricle Using a Combined Bi-Temporal Statistical Model," Fritz et al., Proceedings of SPIE—The International Society for Optical Engineering, Mar. 2006, 6141, DOI10.1117/12.652991.

"Standardized Myocardial Segmentation and Nomenclature for Tomographic Imaging of the Heart. A Statement for Healthcare Professionals from the Cardiac Imaging Committee of the Council on Clinical Cardiology of the American Heart Association," Cerquiera et al., Circulation Jan. 29, 2002;105:539-542.

"Supervised Machine Learning: A Review of Classification Techniques," Kotsiantis et al., Informatica 31, 2007, 249-268.

"Textural Features for Image Classification," Haralick et al., IEEE Transactions on Systems, Man, and Cybernetics, Haralick et al., 1973, SMC-3 (6): 610-621.

EP Office Action and Search Report dated May 31, 2022 of Application No. 18 717 701.9.

Japanese Office Action 1 dated Feb. 2, 2022 of Application No. 2019-552010.

Japanese Office Action 2 dated Jun. 21, 2022 of Application No. 2019-552010.

"Assessment of Myocardial Postreperfusion Viability by Intravenous Myocardial Contrast Echocardiography: Analysis of the Intensity and Texture of Opacification", Ohmori Koji et al., Circulation, Apr. 17, 2001, pp. 2021-2027, XP093147636.

"Automated Identification of Infarcted Myocardium Tissue Characterization Using Ultrasound Images: A Review", Sudarshan Vidya et al., IEEE Reviews in Biomedical Engineering, vol. 8, pp. 86-97, XP011666724.

"Myocardial Contrast Echocardiography: Texture Analysis for Identification of Nonperfused versus Perfused Myocardium", Richard Y Bae et al., Echocardiography, Futura Publishing Co, vol. 18, No. 8, Jul. 28, 2003, pp. 665-672, XP071677424.

EP Office Action dated Apr. 9, 2024 of Application No. 18 717 701.9.

CN Office Action dated Feb. 28, 2024 of Application No. 201880020710.7.

METHOD AND SYSTEM FOR ASSESSING VESSEL OBSTRUCTION BASED ON MACHINE LEARNING

CROSS-REFERENCE TO RELATED APPLICATION(S)

The present application is a continuation-in-part of U.S. application Ser. No. 16/508,996, filed on Jul. 11, 2019, which is a continuation of U.S. application Ser. No. 16/241,165, filed on Jan. 7, 2019, now U.S. Pat. No. 10,395,366, which is a continuation of U.S. application Ser. No. 15/933,854, filed on Mar. 23, 2018, now U.S. Pat. No. 10,176,575, which claims priority from U.S. Provisional App. No. 62/476,382, filed on Mar. 24, 2017, all of which are herein incorporated by reference in their entireties.

BACKGROUND

1. Field

The present application relates generally to methods and systems to assess a severity of vessel obstruction, and methods and systems to form feature-perfusion classification (FPC) models that classify training features in connection with assessing a severity of vessel obstruction.

2. State of the Art

Coronary artery disease (CAD) is one of the leading causes of death worldwide. CAD generally refers to conditions that involve narrowed or blocked blood vessels that can lead to reduced or absent blood supply to the sections distal to the stenosis resulting in reduced oxygen supply to the myocardium, resulting in, for instance, ischemia and chest pain (angina). A very important aspect in the prevention and treatment of CAD is the functional assessment of such narrowed or blocked blood vessels.

Presently, X-ray angiography is the imaging modality used during treatment of stenotic (narrowed) coronary arteries by means of a minimally invasive procedure also known as percutaneous coronary intervention (PCI). During PCI, a (interventional) cardiologist feeds a deflated balloon or other device on a catheter from the inguinal femoral artery or radial artery up through blood vessels until they reach the site of blockage in the artery. X-ray imaging is used to guide the catheter threading. PCI usually involves inflating a balloon to open the artery with the aim to restore unimpeded blood flow. Stents or scaffolds may be placed at the site of the blockage to hold the artery open.

X-ray angiography is also a standard imaging technique for anatomical assessment of the coronary arteries and the diagnosis of coronary artery disease. Although objectivity, reproducibility, and accuracy in assessment of lesion severity has improved by means of quantitative coronary analysis tools (QCA), the physiological significance of atherosclerotic lesions, which is the most important prognostic factor in patients with coronary artery disease, cannot be appreciated by X-ray angiography.

For intermediate coronary lesions (defined as luminal narrowing of 30-70%), for instance, it is not always obvious if the stenosis is a risk for the patient and if it is desired to take action. Overestimation of the severity of the stenosis can cause a treatment which in hindsight would not have been necessary and therefore exposing the patient to risks that are not necessary. Underestimation of the severity of the stenosis, however, could induce risks because the patient is left untreated while the stenosis is in reality severe and actually impedes flow to the myocardium. Especially for these situations it is desired to have an additional functional assessment to aid in a good decision making.

Fractional Flow Reserve (FFR) has been used increasingly over the last 10-15 years as a method to identify and effectively target the coronary lesion most likely to benefit from percutaneous coronary intervention (PCI). FFR is a technique used to measure pressure differences across a coronary artery stenosis to determine the likelihood that the stenosis impedes oxygen delivery to the heart muscle. The technique involves percutaneously inserting a pressure-transducing wire inside the coronary artery and measuring the pressure behind (distal to) and before (proximal to) the lesion. This is best done in a hyperemic state because in the case of maximum hyperemia, blood flow to the myocardium is proportional to the myocardium perfusion pressure. FFR therefore provides a quantitative assessment of the functional severity of the coronary lesion as described in Pijls et al., "Measurement of Fractional Flow Reserve to Assess the Functional Severity of Coronary Artery Stenoses," N Engl J Med 1996, 334:1703-1708.

Although the European Society of Cardiology (ESC) and the American College of Cardiology/American Heart Association (ACC/AHA) guidelines recommend the use of FFR in patients with intermediate coronary stenosis (30-70%), visual assessment, whether or not supported by QCA, of X-ray coronary angiograms alone is still used in over 90% of procedures to select patients for percutaneous coronary intervention (Kleiman et al, "Bringing it all together: integration of physiology with anatomy during cardiac catheterization," J Am Coll Cardiol. 2011; 58:1219-1221).

FFR, however, has some disadvantages. The technique is associated with the additional cost of a pressure wire which can only be used once. Furthermore, measuring FFR requires invasive catheterization with the associated cost and procedure time. Also, in order to induce (maximum) hyperemia, additional drug infusion (adenosine or papaverine) is required, which is an extra burden for the patient.

Coronary computed tomography (CT) angiography (CCTA) is a non-invasive imaging modality for the anatomic assessment of coronary arteries but does not assess the functional significance of coronary lesions. Due to the remarkably high negative predictive value of CCTA and its non-invasive nature, the main strength of CCTA is its excellent ability to exclude CAD. Although CCTA can reliably exclude the presence of significant coronary artery disease, many high-grade stenosis seen on CCTA are not flow limiting. This potential for false positive results has raised concerns that widespread use of CCTA may lead to clinically unnecessary coronary revascularization procedures. This lack of specificity of CCTA is one of the main limitations of CCTA in determining the hemodynamic significance of CAD (Meijboom et al, "Comprehensive assessment of coronary artery stenoses: computed tomography coronary angiography versus conventional coronary angiography and correlation with fractional ow reserve in patients with stable angina," Journal of the American College of Cardiology 52 (8) (2008) 636-643). As a result, CCTA may lead to unnecessary interventions on the patient, which may pose added risks to patients and may result in unnecessary health care costs.

Taylor et al "Computational Fluid Dynamics Applied to Cardiac Computed Tomography for Noninvasive Quantification of Fractional Flow Reserve," Journal of the American College of Cardiology, Vol. 61, No. 22, 2013, and U.S. Pat. No. 8,315,812, describe a noninvasive method for quantifying FFR from CCTA, which we refer to as FFRCT. This technology uses computational fluid dynamics (CFD) applied to CCTA after semi-automated segmentation of the coronary tree including a part of the ascending aorta covering the region in which both the left coronary artery as well as the right coronary artery emanate. Three-dimensional (3D) blood flow and pressure of the coronary arteries are simulated, with blood modeled as an incompressible Newtonian fluid with Navier-Stokes equations and solved subject to appropriate initial and boundary conditions with a finite element method on parallel supercomputer. The FFRCT is modeled for conditions of adenosine-induced hyperemia without adenosine infusion. This process is computationally complex and time-consuming and may require several hours.

There are several limitations for physiologic assessment of coronary stenosis by FFRCT besides its long computation time as mentioned above.

First, FFRCT is calculated by computational simulation of adenosine mediated hyperemia rather than by actual administration of adenosine.

Second, the value of FFRCT is influenced not only by stenosis severity but also by the presence of viable or scarred myocardium (De Caterina et al, "*Limitations of noninvasive measurement of fractional flow reserve from coronary computed tomography angiography*," Journal of the American College of Cardiology, vol. 59, no. 15, pp. 1408-1410, 2012). The status of myocardial microvasculature indicates if a certain portion of the heart can be regarded to be healthy. For instance, the presence of myocardial ischemia is an indication that a certain portion of the heart is not supplied with enough blood for example due to an (earlier) infarction (FIG. 1). This has an effect on the microvascular resistance and should be adjusted accordingly in the model calculations.

Third, the calculated FFRCT values may be lower than compared to FFR values measured invasively in patients with microvascular disease, because modeling of adenosine-induced hyperemia may overestimate the degree of vasodilation (Taylor et al, "*Computational fluid dynamics applied to cardiac computed tomography for noninvasive quantification of fractional flow reserve: scientific basis*," Journal of the American College of Cardiology, vol. 61, no. 22, pp. 2233-2241, 2013).

Fourth, vascular remodeling and collateral flow are not considered and even not visible on CCTA, therefore the assumption is made that no collateral arteries are present which feed the coronary vessel bed distal to the lesion. Collateral flow is an adaptation of the vessels where the collateral vessels provide the myocardium with blood by bypassing the stenotic lesion (FIG. 2). The effect of this is that, even in the case of a very severe stenosis (for instance a total occlusion) the sections distal to the stenosis receive blood flow. Therefore, in practice the effect of the stenosis is not necessarily severe, and a revascularization is not always needed. When collateral flow is present, this also has an effect on the calculations and should also be compensated. However, due to their small size these collateral vessels are not commonly visible on CCTA, and further steps are needed to determine the presence of collateral flow.

Fifth, because FFRCT requires accurate anatomic models, numerous artifacts on CCTA may affect FFRCT calculation, such as blooming artefacts caused by large arterial calcifications and stents. In addition, motion, lower SNR, and mis-registration may compromise its accuracy. Therefore, CCTA data with good image quality is essential for the accuracy of FFRCT interpretation.

In order to keep the computational demands on a feasible level a reduced model can be used in the calculation. Specifically, sections of the coronary tree can be represented by a one-dimensional network or zero-dimensional (lumped) model. This multi-scale approach was adopted by Kim et al, "*Patient-specific modeling of blood flow and pressure in human coronary arteries*," Annals of Biomedical Engineering 38, 3195-3209, 2010 to compute physiologically realistic pressure and flow waveforms in coronary vessels at baseline conditions.

Nickisch et al. "*Learning patient-specific lumped models for interactive coronary blood flow simulations*", International Conference on Medical Image Computing and Computer-Assisted Intervention, Springer, 2015, pp. 433-441, presents a technique to estimate FFR in the coronary artery tree from a CCTA scan, based on blood flow simulations using a parametric patient specific lumped model. This technique is designed to further reduce computational demands. In the aforementioned publication the authors use a hydraulic system analogy to model the coronary tree with an electrical circuit interpretation where volumetric flow rate was modeled as an electrical current and pressure in the coronary artery as a voltage. This technique achieved high accuracy and real-time feedback, but it strongly depends on the segmentation of the coronary artery tree and determination of its centerline. Moreover, the method requires further clinical validation as it was only validated on a small set of CCTA scans.

A different approach to reduce the computation time required by CFD, is introduced in WO2015/058044. In this work, a method is disclosed to assess the FFR by means of a machine learning system which is based on features extracted from the anatomical three-dimensional coronary geometry. The machine-learning is trained by using geometric extracted features from synthetically generated 3D stenosis geometries and FFR values corresponding to the synthetically generated 3D stenosis computed by use of CFD. After the learning phase, the system predicts the FFR based on extraction of the same features of an unseen anatomical three-dimensional coronary geometry which is for instance extracted from CCTA by means of image segmentation methods.

A similar approach is disclosed in US2014/0073977 for assessment of FFR by means of machine-learning algorithm on geometrical features extracted from three-dimensional vessel geometry. In this method the machine learning was performed by extracted 3D coronary tree geometries from patient image data and FFR values corresponding to the patient geometries were computed by CFD.

All of the above described methods heavily rely on the anatomical vessel geometry extracted from the patient's image data. This involves, for assessment of FFR in coronaries, the segmentation of coronary tree. The demands on the segmentation accuracy are high, especially for stenotic segments. Taking into account that a mild coronary obstruction has an average diameter between 1.5-2.5 mm and that spatial resolution of CCTA is in the range of 0.25 mm isotropic, obtaining accurate 3D morphology by means of segmentation is a very challenging task. This in addition to the imaging artifacts induced by calcified coronary atherosclerotic lesions, or other imaging artifacts as discussed before.

Methods to assess the functional significance of a coronary lesion that do not rely on the anatomical coronary vessel geometry combined with blood flow modeling have been developed. For example, George et al. in "*Adenosine stress 64-and 256-row detector computed tomography* angiography and perfusion imaging a pilot study evaluating the transmural extent of perfusion abnormalities to predict atherosclerosis causing myocardial ischemia," Circulation: Cardiovascular Imaging 2 (3) (2009) 174-182, demonstrated that comparison of myocardial regions imaged at rest and pharmacologically-induced stress by administration of adenosine, reveals areas with perfusion defects, which are directly caused by hemodynamically significant stenosis. Although this approach is promising as it merges the anatomic information of CCTA with functional analysis, it requires an additional CT scan which inevitably leads to higher radiation dose and longer examination time and the need for injection of pharmacological stress agents.

There is thus the need for a patient specific method to identify patients with functional significant stenosis in one or more coronary arteries based on the information extracted from a single CCTA dataset only, which has low computational complexity demands and which takes into account the status of the myocardial microvasculature and collateral flow, without relying on the detailed morphology of the coronary arterial system.

SUMMARY OF THE INVENTION

At least one aim of CCTA is to identify cardiac and coronary artery anatomy by means of injecting an exogenous contrast agent, usually via intravenous injection in an antecubital vein to enhance the cardiac and/or coronary anatomy during imaging. According to the Society of Cardiovascular Computed Tomography Guidelines for the performance and acquisition of CCTA as described by Abbara et al. in "*SCCT guidelines for the performance and acquisition of coronary computed tomographic angiography: A report of the Society of Cardiovascular Computed Tomography Guidelines Committee Endorsed by the North American Society for Cardiovascular Imaging (NASCI),*" J Cardiovasc Comput Tomogr. 2016 November-December; 10(6): 435-449, the contrast medium injection is timed in such a way that the coronary arterial system contains sufficient contrast medium to clearly distinguish the coronary artery lumen from surrounding soft tissues. This enables the physician assessment of luminal narrowing as well as coronary artery stenosis with an optimal image quality and thus accuracy. To ensure adequate coronary artery opacification, the aforementioned guidelines describes that CCTA image acquisition is typically started once a pre-defined threshold attenuation value has been reached in a pre-defined anatomical structure (most often this concerns the descending aorta), or by waiting a certain delay time after enhancement is first visible in the ascending aorta. The inventors have furthermore recognized that due to above described method the acquisition of CCTA provides contrast enhancement in the ventricular myocardium, since the injected contrast medium, once it is present in the coronary arteries, will also be delivered to successively smaller generations of coronary arterioles from where it traverses into the coronary microvasculature, which will lead to (subtle) enhancement of the myocardium.

Functionally significant coronary artery stenosis causes ischemia in the ventricular myocardium. Due to the above described acquisition properties of CCTA, there is a difference in myocardial texture characteristics between normal and ischemic parts of the myocardium at the time of CCTA image acquisition.

It is therefore an objective of the present application to perform a patient classification based on machine learning using features of the myocardium.

In embodiments herein, methods and systems are described that present a novel manner to automatically identify patients with functionally significant stenosis in at least one coronary artery, based on the information extracted from a single CCTA dataset. While more than one CCTA dataset may be utilized, only a single dataset is needed. The method first segments the myocardium using for instance a multi-scale CNN trained on manually annotated data. Thereafter, to characterize the left ventricle myocardium, the myocardium characteristics can be derived. This can be done by feature-engineering or by e.g. convolutional autoencoder, or a combination thereof.

Once the characteristics of the myocardium have been extracted, the patients can be classified into those with or without functionally significant stenosis based on these characteristics. This can be done with any classifier (supervised or unsupervised). In a preferred embodiment, patients are classified with a support vector machine (SVM) classifier into those having functionally significant stenosis in one or more of the coronary arteries and those without it, according to invasively determined FFR measurements that are the current reference standard.

In accordance with aspects herein, a method is provided for assessing the presence of functionally significant stenosis in one or more coronary arteries, further known as a severity of vessel obstruction. The method assesses if patients suffers from significant coronary obstructions, without differentiating which particular obstruction is responsible for a particular functional significant coronary obstruction. The method can implement a prediction phase that includes: obtaining a contrast enhanced volume image dataset for a target organ; segmenting at least a portion of the volume image data set into data segments corresponding to wall regions of the target organ; analyzing the data segments to extract features that are indicative of an amount of perfusion experiences by wall regions of the target organ; obtaining a feature-perfusion classification (FPC) model derived from a training set of perfused organs; classifying of the data segments based on the features extracted and based on the FPC model; and providing, as an output, a prediction indicative of a severity of vessel obstruction based on the classification of the features.

In accordance with aspects herein, the FPC model can represent the relationship between training features and reference fluidodynamic parameters indicative of baseline amounts of vessel perfusion for corresponding wall regions of the training set of perfused organs.

In accordance with aspects herein, the reference fluidodynamic parameter can represent an invasive fractional flow reserve measurement.

In accordance with aspects herein, the features can be texture and/or morphologic features.

In accordance with aspects herein, the features can be determined using a convolutional auto-encoder, Gaussian filters, transmural perfusion ratio, Haralick features, myocardium thickness or shape of the target organ.

In accordance with aspects herein, the organ can be the myocardium and the vessels the coronary arteries.

In accordance with aspects herein, the classifying operation can utilize secondary information to perform the classification. The secondary information can include one or more of the following parameters: coronary tree anatomy, demographic information of the patient, coronary artery calcification, coronary plaque, spectral multi-energy or photon counting, ECG parameters, cardiac biomarkers, adipose tissue surrounding or within the heart, shape of myocardium, or the like.

In accordance with aspects herein, the analyzing operation can include extracting, for each of the data segments, a feature vector that comprises multiple factors that are measured or extracted from the corresponding data segment, wherein the multiple factors describe or characterize a nature of the corresponding wall region.

In accordance with aspects herein, the FPC model can be obtained from a database of contrast enhanced volume image data sets and associated training feature vectors extracted from the contrast enhanced volume image data sets, where the training feature vectors include known labels. The classifying operation can utilize a machine-learning algorithm that is trained based on the known labels, where the machine-learning algorithm classifies the data segments based on the features.

In accordance with aspects herein, the indication that is output can indicate severity of the vessel obstruction relative to a training vessel obstruction.

In accordance with aspects herein, the method further comprises implementing a training phase to form the FPC model that classifies training features for the training set of perfused organs from contrast enhanced volume image datasets of the organ of the training set and a reference fluidodynamic parameter related to a vessel or vessels perfusing the organs. The training phase can include: providing contrast enhanced volume image datasets of each of the organs in the training set; segmenting the organs of the training set; analyzing the data segments to extract training features that are indicative of an amount of perfusion experiences by wall regions of the organs of the training set; and classifying the training features of the organs of the training set relative to reference fluidodynamic parameters indicative of baseline amounts of vessel perfusion for corresponding regions of the training set of perfused organs to form the FPC model.

In accordance with aspects herein, the method can further include clustering the features or training features extracted before performing the classifying operations in the training phase and/or in the prediction phase.

In accordance with aspects herein, the analyzing can extract a feature vector comprising a series of factors, where each of the factors has a value representing an amount of variation in a characteristic of interest over multiple clusters.

In accordance with aspects herein, a method is provided to form a feature-perfusion classification (FPC) model that classifies training features in connection with assessing a severity of vessel obstruction. The method can include: a) obtaining a contrast enhanced volume image dataset for a training perfused organ; b) segmenting at least a portion of the volume image data set into data segments corresponding to wall regions of the perfused target organ; c) analyzing the data segments to extract training features that are indicative of an amount of perfusion experiences by wall regions of the training perfused organ; d) classifying the training features of the training perfused organ relative to reference fluidodynamic parameters indicative of baseline amounts of vessel perfusion for corresponding regions of the training perfused organ to form the FPC model.

In accordance with aspects herein, a system is provided for assessing a severity of vessel obstruction, which includes: memory configured to store a contrast enhanced volume image dataset for a target organ; one or more processors that, when executing program instructions stored in the memory, are configured to: a) segment at least a portion of the volume image data set into data segments corresponding to wall regions of the target organ; b) analyze the data segments to extract features that are indicative of an amount of perfusion experiences by wall regions of the target organ; c) obtain a feature-perfusion classification (FPC) model derived from a training set of perfused organs; d) classify of the data segments based on the features extracted and based on the FPC model; and e) provide, as an output, a prediction indicative of a severity of vessel obstruction based on the classification of the features.

In accordance with aspects herein, the FPC model can represent a relationship between training features and reference fluidodynamic parameters indicative of baseline amounts of vessel perfusion for corresponding regions of the training set of perfused organs.

In accordance with aspects herein, the reference fluidodynamic parameter can represent an invasive fractional flow reserve measurement.

In accordance with aspects herein, the one or more processors can be configured to perform classifying operation by utilizing secondary information to perform the classification. The secondary information can include one or more of the following parameters: coronary tree anatomy, demographic information of the patient, coronary artery calcification, coronary plaque, spectral multi-energy or photon counting, ECG parameters, cardiac biomarkers, adipose tissue surrounding or within the heart, shape of myocardium, or the like.

In accordance with aspects herein, the one or more processors can be configured to perform the analyzing operation by extracting, for each of the data segments, a feature vector that comprises multiple factors that are measured or extracted from the corresponding data segment, wherein the multiple factors describe or characterize a nature of the corresponding region.

In accordance with aspects herein, the one or more processors can be configured to extract a feature vector comprising a series of factors, where each of the factors has a value representing an amount of variation in a characteristic of interest over multiple clusters.

In accordance with aspects herein, the one or more processors can be configured to extract a feature vector comprising a series of factors, where each of the factors represents an intensity of a characteristic of interest over multiple segments of the myocardium.

In accordance with aspects herein, the one or more processors can be configured to extract a feature vector comprising a series of factors, where a subset of the factors in the series represent intensity within segments, and where another subset of the factors in the series represent values indicative of myocardium volume, minimum myocardium thickness and/or maximum myocardium thickness.

BRIEF DESCRIPTION OF THE DRAWINGS

The characteristics of the present application and the advantages derived therefrom will be more apparent from the following description of non-limiting embodiments, illustrated in the annexed drawings.

DETAILED DESCRIPTION OF EMBODIMENTS

Figure 1:
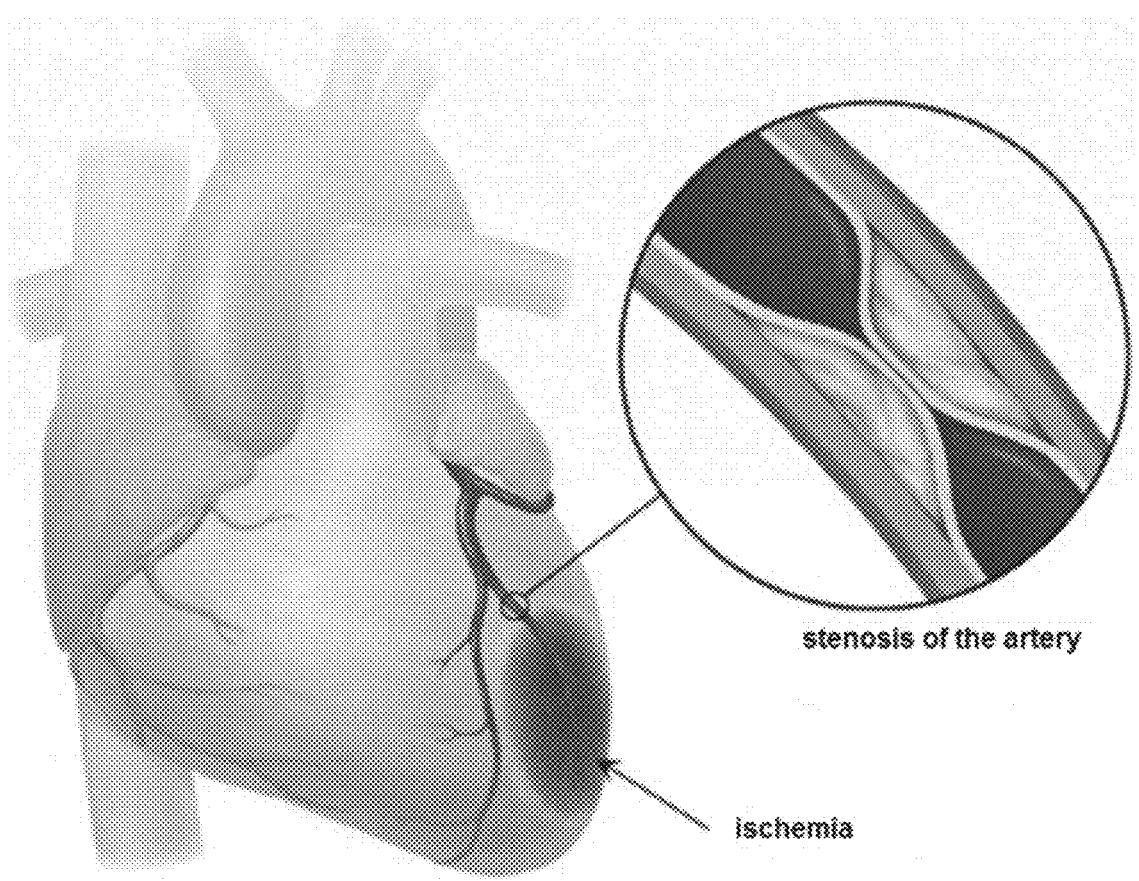
FIG. 1 shows an example of ischemia due to a stenosis of an artery.

The term "unseen", as used throughout, refers to "non-training" items. For example, an unseen image is not a training image, an unseen feature is not a training feature. Instead, the unseen features, images, geometries, and other unseen items refer to aspects of a patient or object of interest that is being analyzed during the prediction phase of operation.

The present application relates to a method and system for machine learning to assess the hemodynamic functional severity of one or more vessel obstructions of a target organ based on contrast enhanced volumetric image dataset. In a preferred embodiment, the target organ represents the myocardium and the vessels the coronary arteries. A functionally significant stenosis is a hemodynamically significant obstruction of a vessel, and with respect to coronary arteries it defines the likelihood that coronary artery obstruction(s) impedes oxygen delivery to the heart muscle and causes anginal symptoms. Fractional flow reserve is a hemodynamic index for assessment of functionally significant coronary artery obstruction(s). In addition to fractional flow reserve, other hemodynamic indices can be used to assess functionally significant coronary artery obstruction(s), such as coronary flow reserve, instantaneous wave-free ratio, hyperemic myocardium perfusion, index of microcirculatory resistance and pressure drop along a coronary artery.

Embodiments of the present application utilize machine learning to determine the presents of functional significant stenosis in one or more coronary arteries from a CCTA dataset. Machine learning is a subfield of computer science that "gives computers the ability to learn without being explicitly programmed". Evolved from the study of pattern recognition and computational learning theory in artificial intelligence, machine-learning explores the study and construction of algorithms that can learn from and make predictions on data—such algorithms overcome following strictly static program instructions by making data driven predictions or decisions, through building a model from sample inputs. Machine-learning is employed in a range of computing tasks where designing and programming explicit algorithms is infeasible.

Given a dataset of images with known class labels, machine-learning system can predict the class labels of new images. There are at least two parts to any such system. The first part of the machine-learning is a feature extraction (extractor), being an algorithm for creating a feature vector given an image. A feature vector comprises a series of factors (e.g. multiple numbers) that are measured or extracted from the image dataset(s), which describe or characterize the nature of the corresponding wall region of the image. These features are then used by the second part of the system, a classifier, to classify unseen feature vectors extracted from the unseen image. Given a (large) database of images and extracted feature vectors whose labels are known and were used beforehand to train the machine-learning algorithm, classifying unseen images based on the features extracted the same way as in images with (known) labels (training images) is possible.

Figure 3:
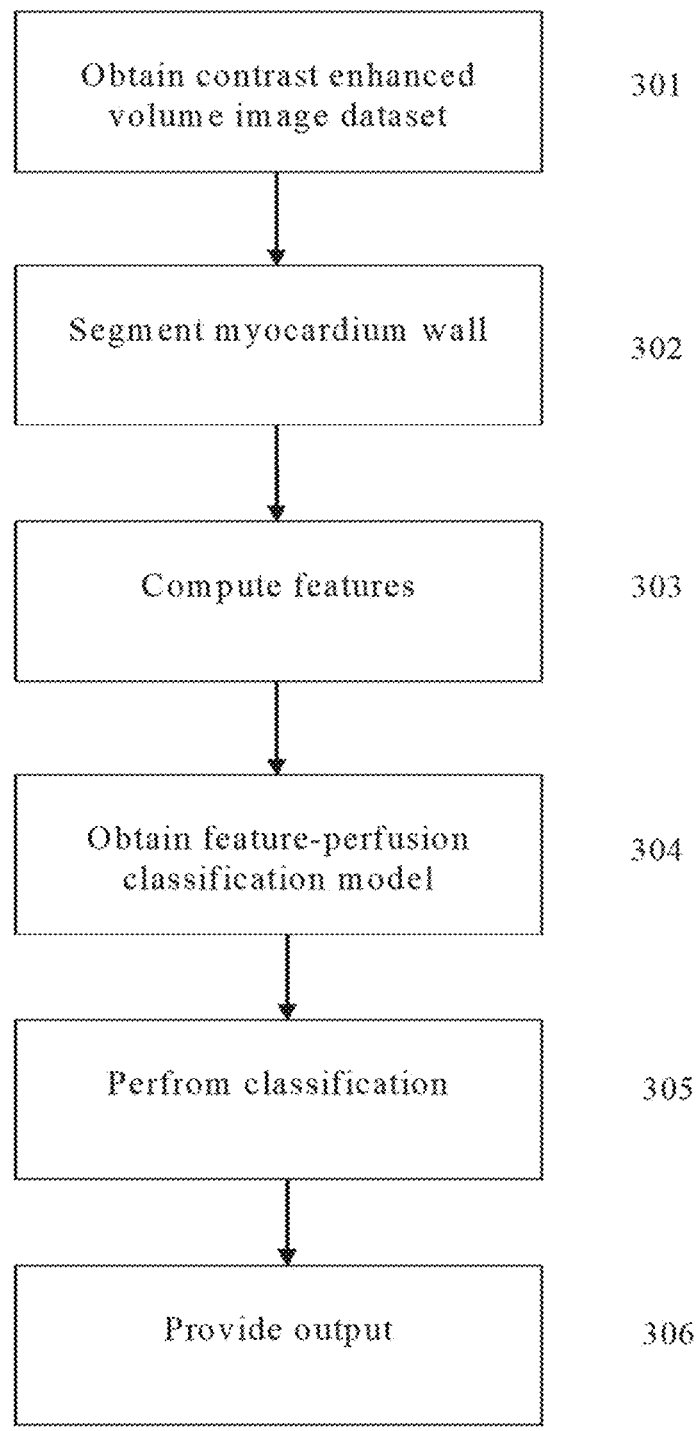
FIG. 3 shows illustrates a flowchart of a machine learning based method for determining the presents of functional significant stenosis in one or more coronary arteries to an embodiment of the present invention.

FIG. 3 shows a flow chart illustrating the operations according to an embodiment of the present application. The operations employ an imaging system capable of acquiring and processing CCTA dataset of an organ (or portion thereof) or other object of interest.

Figure 4:
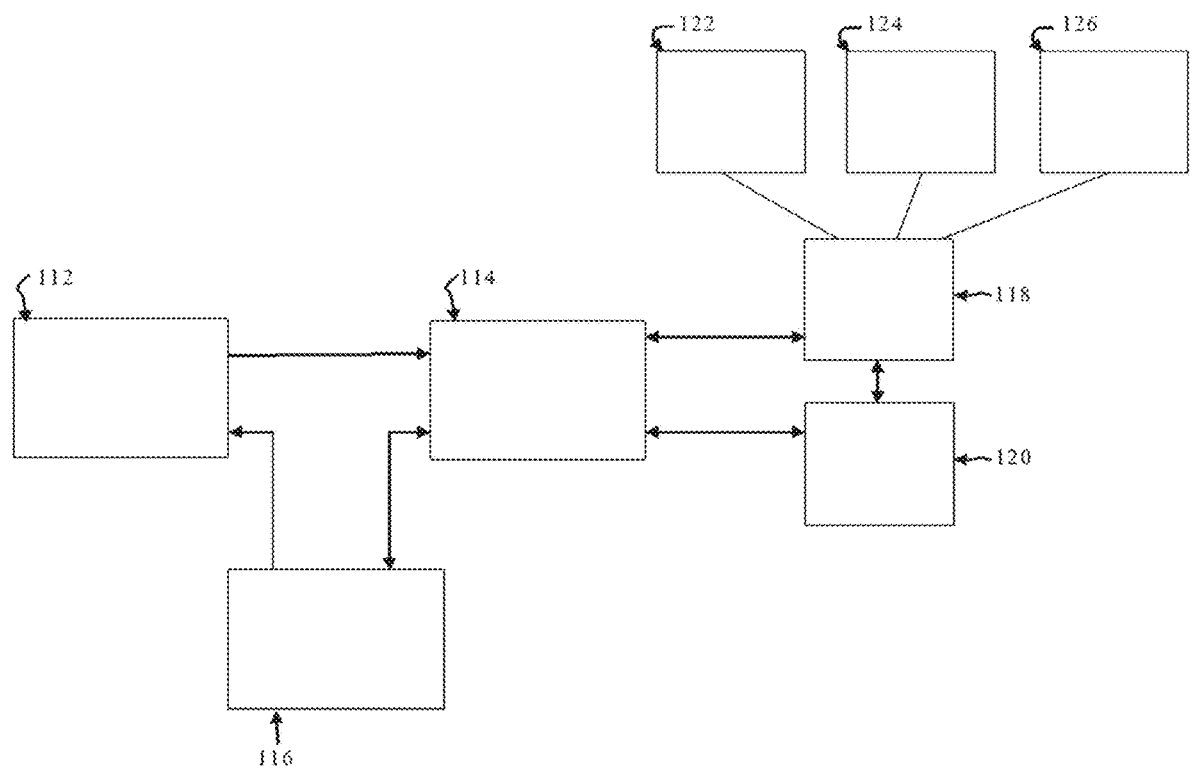
FIG. 4 shows a functional block diagram of an exemplary CT system.

FIG. 4 is a functional block diagram of an exemplary CT system, which includes a CT imaging apparatus 112 that operates under commands from user interface module 116 and will provide data to data processing module 114.

The CT imaging apparatus 112 captures a CT scan of the organ of interest. The CT imaging apparatus 112 typically includes an X-ray source and multi detector mounted in a rotatable gantry. The gantry provides for rotating the X-ray source and detector at a continuous speed during the scan around the patient who is supported on a table between the X-ray source and detector.

The data processing module 114 may be realized by a personal computer, workstation, or other computer processing system. The data processing module 114 processes the CT scan captured by the CT imaging apparatus 112 to generate data as described herein. The user interface module 116 interacts with the user and communicates with the data processing module 114. The user interface module 116 can include different kinds of input and output devices, such as a display screen for visual output, a touch screen for touch input, a mouse pointer or other pointing device for input, a microphone for speech input, a speaker for audio output, a keyboard and/or keypad for input, etc. The data processing module 114 and the user interface module 116 cooperate to carry out the operations of the processes described herein.

The data processing module 114 includes one or more memory 118 and one or more processors 120. The memory 118 stores, among other things, the contrast enhanced volume dataset for the target organ, data segments, features extracted from analysis of the data segments, one or more FPC models, classifications for the data segments and predictions indicative of a severity of vessel obstruction. The memory 118 may also store one or more contrast enhanced volume datasets for the training perfused organs, data segments corresponding to the wall regions of the perfused target organs, training features extracted from analysis of the training data segments, classifications for the training features, one or more FPC models, and known labels. The memory 118 also stores software code that directs the one or more processors 120 to carry out the operations of the processes described herein. For example, the memory 118 may include an optical disc or other form of persistent memory such as a USB drive or a network server. The software code can be directly loadable into the memory of a data processing module 114 for carrying out the operations described herein.

In accordance with aspects herein, the imaging system has previously acquired and stored at least one CCTA dataset of an object of interest. Any imaging device capable of providing a CT scan can be used for this purpose. In accordance with aspects herein, the one or more processors 120 of the data processing module 114 implement a method for assessing a severity of vessel obstruction, the method implementing a prediction phase that comprises: obtaining a contrast enhanced volume image dataset for a target organ; segmenting at least a portion of the volume image data set into data segments corresponding to wall regions of the target organ; analyzing the data segments to extract features that are indicative of an amount of perfusion experiences by wall regions of the target organ; obtaining a feature-perfusion classification (FPC) model derived from a training set of perfused organs; classifying of the data segments based on the features extracted and based on the FPC model; and providing, as an output, a prediction indicative of a severity of vessel obstruction based on the classification of the features.

The memory 118 may store one or more FPC models 122 and reference fluidodynamic parameters 124. The FPC models 122 include a relationship between training features and the reference fluidodynamic parameters 124 indicative of baseline amounts of vessel perfusion for corresponding wall regions of the training set of perfused organs. For example, the relationship may be "functionally significant stenosis present" or "no significant stenosis present". In case of two classes. Optionally, non-limiting examples of other relationships include "no functionally significant stenosis present", "mild functionally significant stenosis present" or "severe functionally significant stenosis present." The reference fluidodynamic parameters 124 may comprise an invasive fractional flow reserve measurement. The memory 118 stores the features 126 that are extracted from the data segments. The features 126 texture and/or morphologic features that are descriptive of a texture or morphology of the corresponding wall region.

For example, the processors 120 may determine the features using a convolutional auto-encoder, Gaussian filters, transmural perfusion ratio, Haralick features, myocardium thickness or shape of the target organ. The processors 120 may perform the classifying operation utilizing secondary information. For example, the secondary information may comprise one or more of the following parameters: coronary tree anatomy, demographic information of the patient, coronary artery calcification, coronary plaque, spectral multi-energy or photon counting, ECG parameters, cardiac biomarkers, adipose tissue surrounding or within the heart, shape of myocardium, or the like.

The processors 120 perform the analyzing operation by extracting, for each of the data segments, a feature vector that comprises multiple factors that are measured or extracted from the corresponding data segment, wherein the multiple factors describe or characterize a nature of the corresponding wall region. The processors 120 obtain the FPC model from a data base of contrast enhanced volume image data sets and associated training feature vectors extracted from the contrast enhanced volume image data sets, the training feature vectors including known labels, wherein the classifying operation utilizes a machine-learning algorithm that is trained based on the known labels, the machine-learning algorithm classifying the data segments based on the features.

The processor 120 implement a training phase to form the FPC model that classifies training features for the training set of perfused organs from contrast enhanced volume image datasets of the organ of the training set and a reference fluidodynamic parameter related to a vessel or vessels perfusing the organs, the training phase comprising: providing contrast enhanced volume image datasets of each of the organs in the training set; segmenting the organs of the training set; analyzing the data segments to extract training features that are indicative of an amount of perfusion experiences by wall regions of the organs of the training set; and classifying the training features of the organs of the training set relative to reference fluidodynamic parameters indicative of baseline amounts of vessel perfusion for corresponding regions of the training set of perfused organs to form the FPC model.

The processor 120 cluster the features or training features extracted before performing the classifying operations in the training phase and/or in the prediction phase. In accordance with aspects herein, the processor 120 extract, as the features, a feature vector comprising a series of factors, where each of the factors has a value representing an amount of variation in a characteristic of interest over multiple clusters.

In accordance with aspects herein, the processors 120 form a feature-perfusion classification (FPC) model that classifies training features in connection with assessing a severity of vessel obstruction, the method comprises: a) obtaining a contrast enhanced volume image dataset for a training perfused organ; b) segmenting at least a portion of the volume image data set into data segments corresponding to wall regions of the perfused target organ; c) analyzing the data segments to extract training features that are indicative of an amount of perfusion experiences by wall regions of the training perfused organ; d) classifying the training features of the training perfused organ relative to reference fluidodynamic parameters indicative of baseline amounts of vessel perfusion for corresponding regions of the training perfused organ to form the FPC model.

In accordance with aspects herein, the processors 120 assess a severity of vessel obstruction, by executing program instructions stored in the memory, to: a) segment at least a portion of the volume image data set into data segments corresponding to wall regions of the target organ; b) analyze the data segments to extract features that are indicative of an amount of perfusion experiences by wall regions of the target organ; c) obtain a feature-perfusion classification (FPC) model derived from a training set of perfused organs; d) classify of the data segments based on the features extracted and based on the FPC model; and e) provide, as an output, a prediction indicative of a severity of vessel obstruction based on the classification of the features.

In accordance with aspects herein, the processors 120 are configured to perform the analyzing operation by extracting, for each of the data segments, a feature vector that comprises multiple factors that are measured or extracted from the corresponding data segment, wherein the multiple factors describe or characterize a nature of the corresponding region. In accordance with aspects herein, the processors 120 are configured to extract, as the features, a feature vector comprising a series of factors, where each of the factors has a value representing an amount of variation in a characteristic of interest over multiple clusters. In accordance with aspects herein, the processors 120 are configured to extract, as the features, a feature vector comprising a series of factors, where each of the factors represents an intensity of a characteristic of interest over multiple segments of the myocardium. In accordance with aspects herein, the processors 120 are configured to extract, as the features, a feature vector comprising a series of factors, where a subset of the factors in the series represent intensity within segments, and where another subset of the factors in the series represent values indicative of myocardium volume, minimum myocardium thickness and/or maximum myocardium thickness.

The operations of FIG. 3 can also be carried out by software code that is embodied in a computer product (for example, an optical disc or other form of persistent memory such as a USB drive or a network server). The software code can be directly loadable into the memory of a data processing system for carrying out the operations of FIG. 3.

In this example it is assumed that the imaging system has acquired and stored at least one CCTA dataset of an object of interest. Any imaging device capable of providing a CT scan can be used for this purpose.

The present application is particularly advantageous in myocardium analysis based on CCTA dataset and it will mainly be disclosed with reference to this field, particularly for patient classification.

An embodiment of the present application is now disclosed with reference to FIG. 3. The therein-depicted steps can, obviously, be performed in any logical sequence and can be omitted in parts.

As described in step 301 of FIG. 3, a contrast enhanced CCTA dataset is obtained. This CCTA dataset can be obtained from a digital storage database, such as a picture archiving and communication system (PACS) or a VNA (vendor neutral archive), a local digital storage database, a cloud database, or acquired directly from a CT imaging modality. During the CCTA imaging, a contrast agent was induced in the patient. Furthermore, the CCTA imaging can be ECG triggered.

Figure 5:
FIG. 5 shows an example of an end result of a Left Ventricle myocardium segmentation.

To identify patients with functionally significant stenosis, the left ventricle (LV) and/or right ventricle (RV) myocardium wall needs to be segmented in the CCTA dataset as depicted in step 302 of FIG. 3. This can be done manually by the user or by (semi)automatic segmentation. One example of an automatic segmentation of the LV myocardium is given by Zreik et. al., "*Automatic segmentation of the left ventricle in cardiac ct angiography using convolution neural networks,*" 2016 IEEE 13*th* International Symposium on Biomedical Imaging (ISBI), 2016, pp 40-43. Zreik et. al. discloses a method in which the myocardium is automatically segmented using a convolutional neural network (CNN) trained on manually annotated data. At the end of this step a segmentation of the myocardium is present. An example of such a myocardium segmentation is shown in FIG. 5, which shows the segmented LV myocardium in an axial, sagittal and coronal CCTA image slice.

Figure 2:
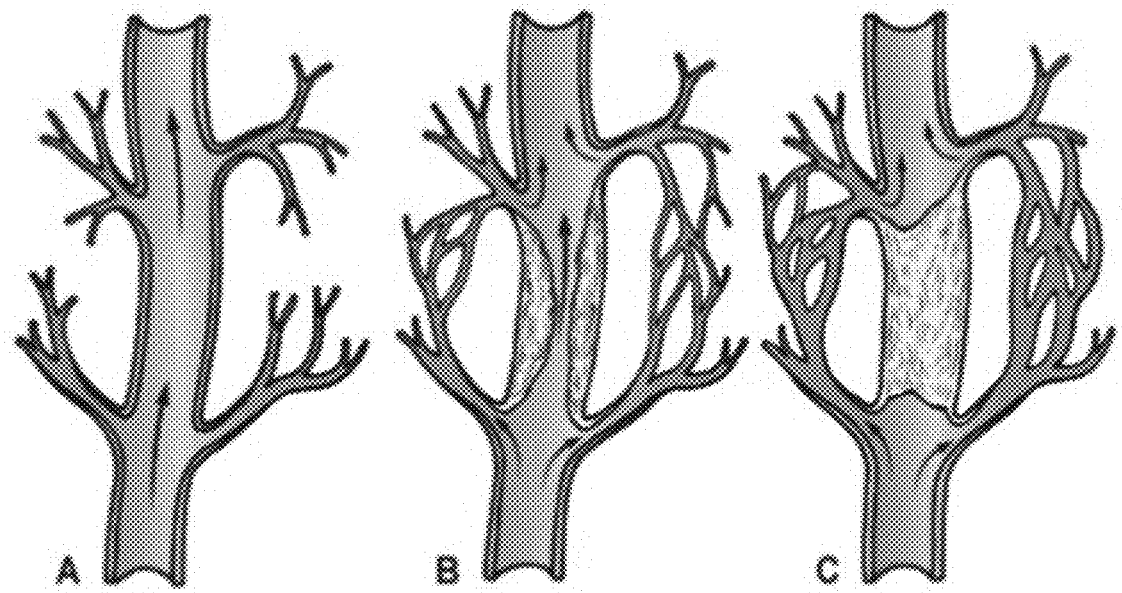
FIG. 2 shows an example of collateral flow across a lesion.

Functionally significant coronary artery stenosis causes ischemia in the myocardium which impacts the texture characteristics of the myocardium wall in a CCTA dataset. Hence, by describing the myocardium, ischemic changed could be captured. Step 303 of FIG. 3, the features characterizing the myocardium are computed from the CCTA dataset. To learn the features characterizing the myocardium, machine-learning is utilized. Step 304 of FIG. 3 a machine learned feature-perfusion classification model is obtained. This model is generated during a training phase. In the training phase the relationship between features and a reference standard is learned. The reference value can represent a fluidodynamic parameter, such as FFR. The features extracted in step 303 of FIG. 3 are designed to recognize (hidden) patterns, such as texture patterns, within the myocardium that correlates to functionally significant coronary obstruction(s). This design of extraction features directly from the myocardium covers two important elements for the assessment of hemodynamic significant lesion(s) that are not considered in prior art. First, collateral arteries, which provide blood flow to the myocardium by bypassing the obstruction (FIG. 2) is automatically taken into consideration. Second, myocardium microvasculature disease such as presence of ischemia (FIG. 1) is automatically taken into consideration.

Step 305 of FIG. 3 assessed the severity of coronary vessel obstruction(s) of an unseen CCTA dataset by classifying the unseen CCTA dataset (prediction phase) based on the learned feature-perfusion model within step 304 of FIG. 3. The output (step 306 of FIG. 3) is a prediction indicative of the likelihood of a functional significant coronary obstruction is present.

Figure 6:
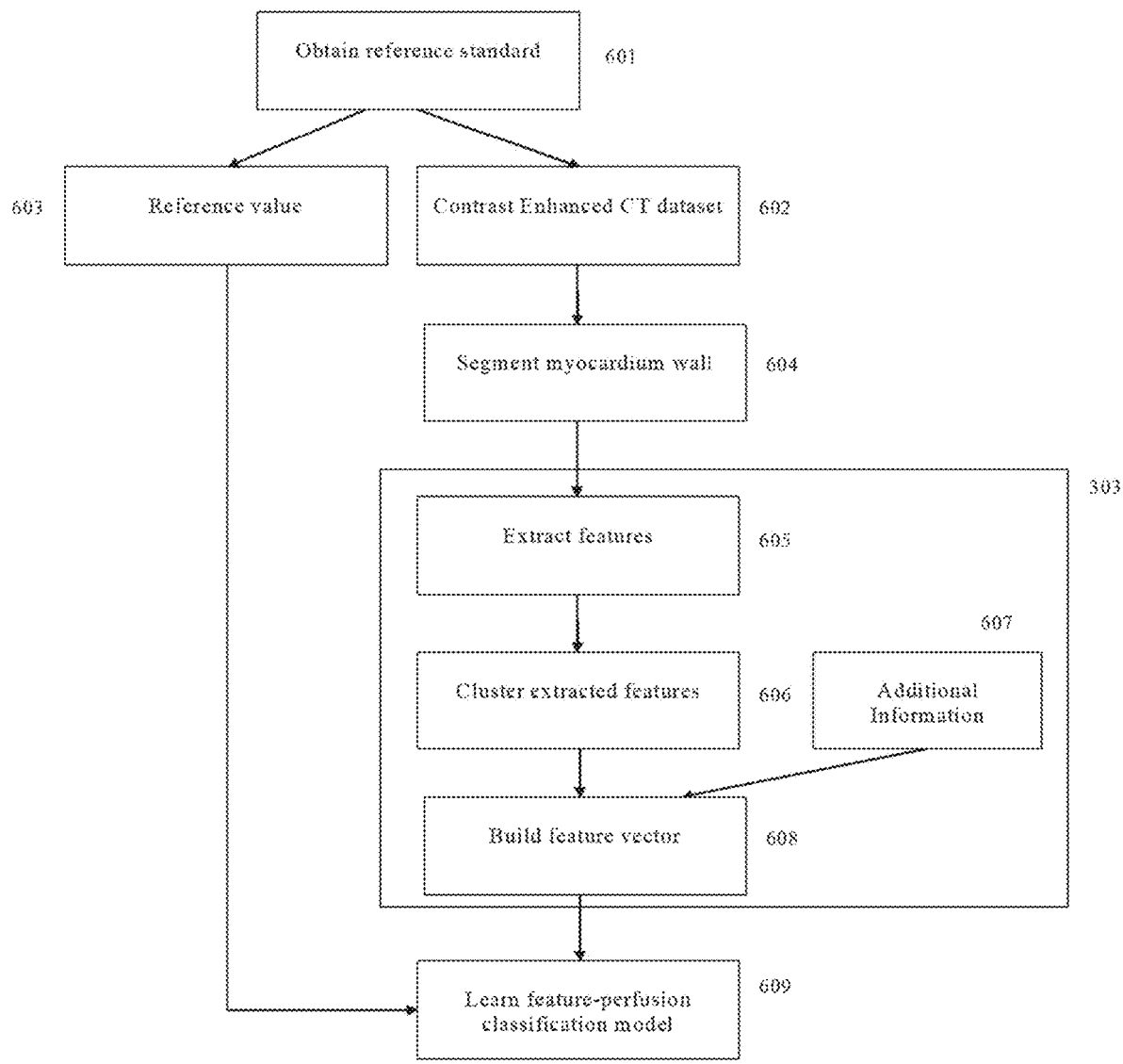
FIG. 6 shows a flowchart of the generation of the feature-perfusion classification model as performed by the training phase.

FIG. 6 illustrates a framework for implementing the feature-perfusion classification model as described by step 304 of FIG. 3. FIG. 6 illustrates the training phase of the system. In step 601 of FIG. 6 the reference standard is obtained as used to train the feature-perfusion classification model. The reference standard is a database which contains data of multiple patients. Each set within this database contains for each patient a) contrast enhanced CT datasets (step 602) with belonging b) invasively measured fractional flow reserve reference values (step 603). Features extracted during the training phase are also known as training features.

Step 604 of FIG. 6 segments the myocardium wall and is identical to step 302 of FIG. 3. Block 303 within FIG. 6 represents step 303, the definition of the features, of FIG. 3 and will be explained in more detail with reference to FIG. 6.

Within step 605 of FIG. 6, the features characterizing the myocardium are extracted from the CCTA dataset. Even though the myocardium is contrast enhanced, these changes are mostly subtle, and it would be extremely challenging—if not impossible in the case of smaller perfusion defects—to manually label myocardial voxels affected by ischemia. In a preferred embodiment, the myocardium is characterized by the features in an unsupervised manner, extracted via encodings, as determined by a convolutional autoencoder (CAE). Alternative, any other engineered characteristic that describes myocardium texture (e.g. Gaussian filters, Haralick texture features) and/or morphology (e.g. myocardium thickness, myocardium volume, ventricular volume but also shape of the heart itself) can be used as features. An example of such alternative engineered feature method designed to quantify the perceived texture of the myocardium is by computing Haralick texture features, which captures numerical features of a texture using spatial relations of similar gray tones (Robert M. Haralick et al., "*Textural*

Features for Image Classification," IEEE Transactions on Systems, Man, and Cybernetics, 1973, SMC-3 (6): 610-621). Another example of such an alternative engineered feature method is the transmural perfusion ratio which defines the ratio of perfusion (or Hounsfield values) between the endocardial and epicardial layers of the myocardium (Arbab-Zadeh et al., "*Adenosine stress 64-and 256-row detector computed tomography angiography and perfusion imaging: a pilot study evaluating the transmural extent of perfusion abnormalities to predict atherosclerosis causing myocardial ischemia*," Circ Cardiovasc Imaging. 2009 May; 2(3):174-82). Any combination of these features can be selected. If the features are local (e.g. per voxel, supervoxel or in same way defined cluster of voxel), dimensionality reduction is needed to represent the patient myocardium instead of its voxels, for instance by clustering and using higher order statistics on the cluster as features.

In a preferred embodiment, the myocardium is characterized by the features in an unsupervised manner, extracted via encodings, as determined by a CAE (Goodfellow, et. al., "*Deep Learning (Adaptive Computation and Machine Learning series)*," Nov. 18, 2016, ISBN 10: 0262035618). A CAE compress all the data from an input image to a small vector from which it must contain enough information to reconstruct the input image by the decoder. By this the autoencoder is forced to learn features about the image being compressed. A typical CAE contains of two major parts, an encoder and a decoder. The CAE compresses (encodes) the data to lower dimensional representations by convolutional operations and max-pooling, and subsequently expands (decodes) the compressed form to reconstruct the input data by deconvolutional operations and unpooling.

Figure 7:
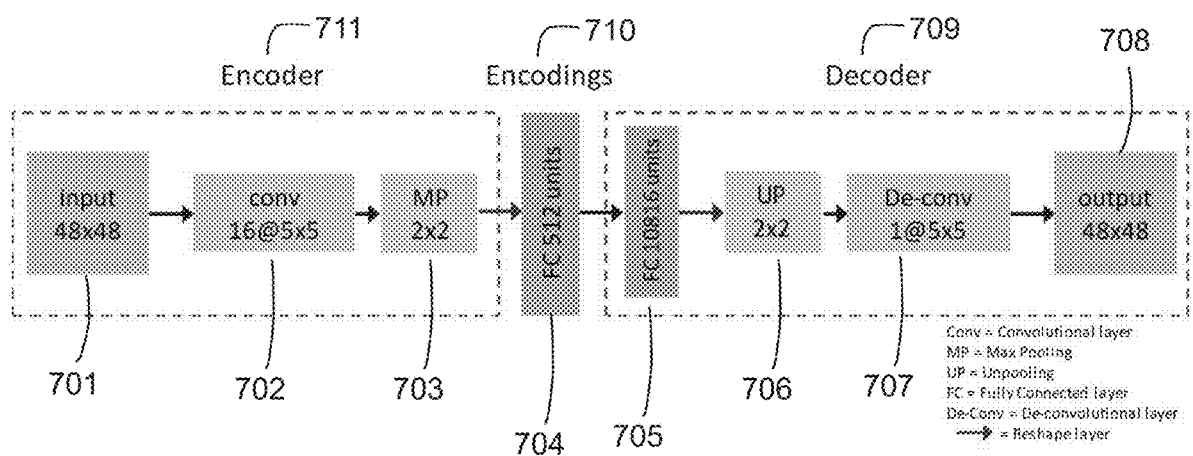
FIG. 7 shows an example of the architecture of a convolution auto encoder (CAE) as used during learning the CAE.

The CAE architecture used in this embodiment is shown in FIG. 7. The CAE architecture presented in FIG. 7 should be considered as an example, and other CAE architectures can be deployed. The encoder (711) e.g. comprises of one convolutional and one max-pooling layer, compressing the input and one fully connected layer providing the encodings. The decoder (709) comprises of one fully connected layer, as well as one unpooling and one deconvolution layers providing the reconstructed input. Nonlinearity is applied to the output of each layer to enable the CAE to handle more complex data. For example, Exponential Linear Unit (ELU) (Clevert et al., "*Fast and accurate deep network learning by exponential linear units (ELUs)*," in: International Conference on Learning Representations, 2016") can be used as nonlinear activation function in all layers except the output layer, where nonlinearity is not applied.

The detailed CAE architecture, as presented by FIG. 7, has the following design: The size of the input of the CAE was set to 48×48 voxels patches. The CAE comprised of one convolutional layer with 16 kernels of 5×5 (702) and one 2×2 max-pooling layer (703), followed by the encoding layer of one fully connected layer with 512 units (704 FIG. 7, representing the number of encodings, N). The generated encodings served as the input of the decoder part, which comprised of one fully connected layer with 10816 units (705), one 2×2 unpooling layer (706) followed by one deconvolution layer with a single 5×5 kernel (707). Other parameters can be used, for instance different kernel sizes, number of encoding layers as well as other CAE architectures and activation functions. Furthermore, the input size of the CAE can be different as well of the use of a 3D input patch (volume), or even 4D input patch for instance to support multiphase CCTA datasets. The input patch can even be a higher dimensional input patch, for instance n-dimensional to support multi-energy CCTA dataset. Learning of the CAE is performed in an unsupervised manner such that extracted features (encodings in case of CAE) describe and characterize the myocardium within the CCTA dataset. This unsupervised learning of the CAE is performed by using the CCTA datasets (602) within the reference standard (601). From each CCTA dataset patches are extracted around randomly selected myocardium voxels within the segmented myocardium as a result of step 604.

Figure 8:
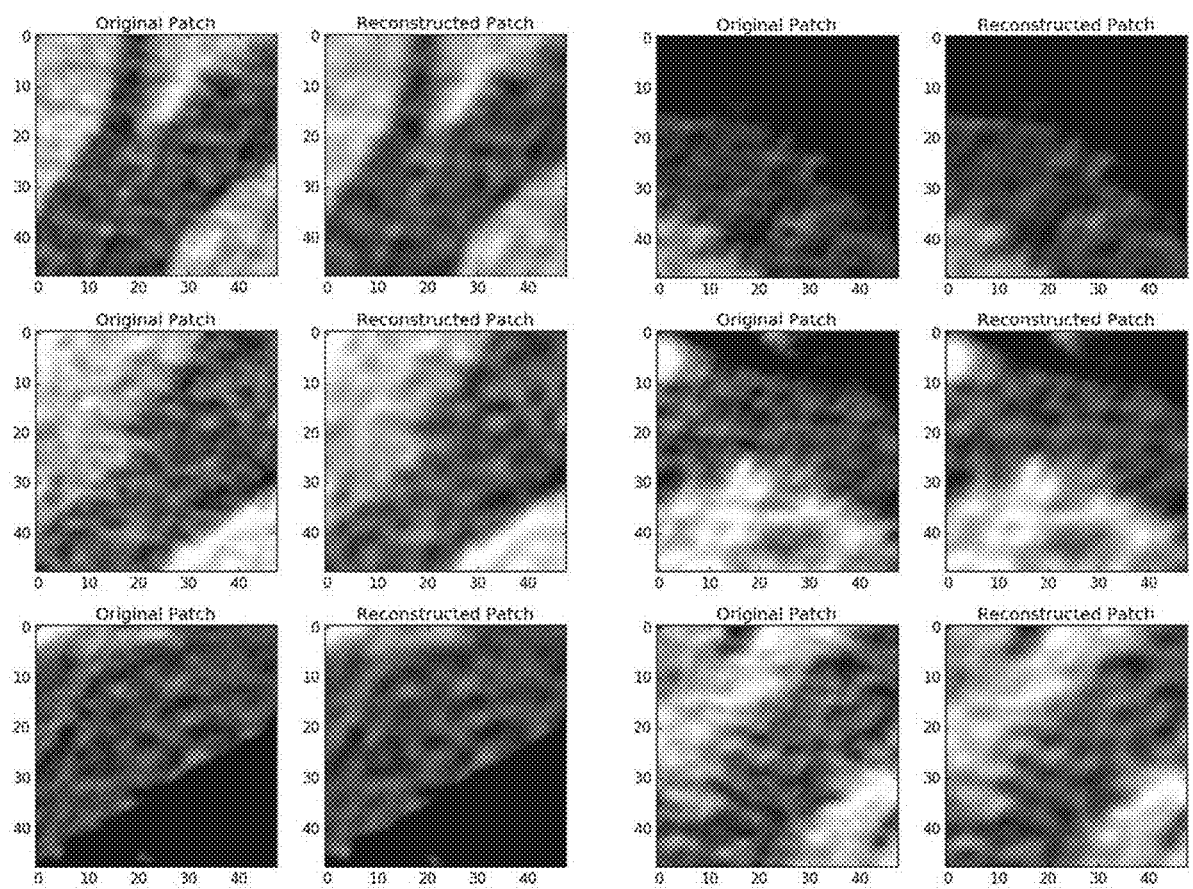
FIG. 8 shows six examples of reconstructed patches. Each row contains 2 pairs of patches, each pair contains the original input patch (right) and the reconstructed output patch (left).

During training, the CAE compress (encodes) input image (701) to a small vector of numbers (encodings, 710) and subsequently expands (decodes) the compressed form (output, 708) to reconstruct the input image. The CAE is trained by comparing the reconstructed output image (708) and the input image (701) in an iterative process to minimize the difference between them. The difference between the input image (input of the encoder, 701 of FIG. 7) and the reconstructed output image (output of the decoder, 706 of FIG. 7) may be determined by the mean squared error and is iteratively minimized by for instance the Stochastic Gradient Descent (SGD) with Nesterov momentum as described by Y. Nesterov, et al. "*Gradient methods for minimizing composite objective function*," Tech. rep., UCL (2007). In each iteration, convolutional filters (702 and 703) are adjusted and updated. This iterative process stops when the mean squared error is within a predefined value. The result of this process ensures that abstract features (encodings) are produced from the input image (701) that contains enough information to reconstruct that input image. FIG. 8 illustrates six different pairs of, for example 48×48, input patches (701 of FIG. 7) and the corresponding reconstructed patches (708 of FIG. 7), which were reconstructed using the trained CAE.

Once the CAE is trained, the decoder part (709 of FIG. 7) is removed, and the fully connected layer (710 of FIG. 7) becomes the output layer which is used to generate encodings for unseen patches.

Figure 9:
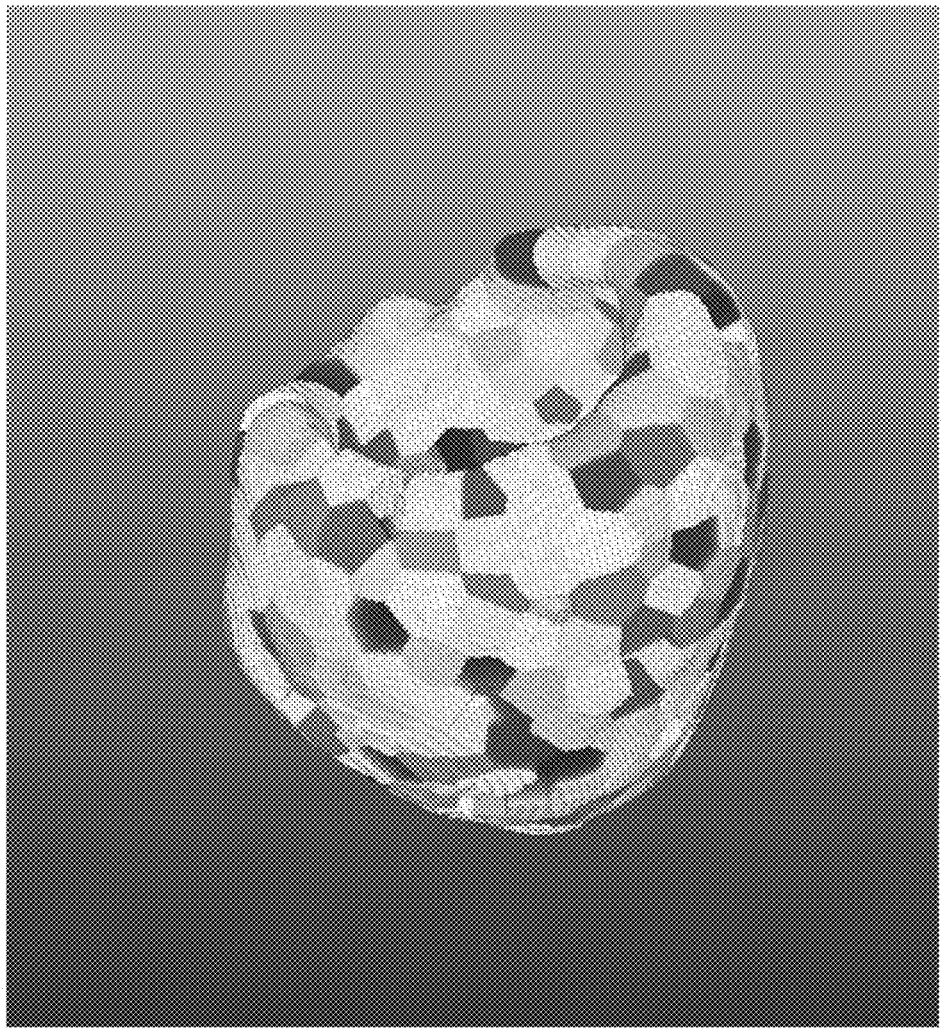
FIG. 9 shows an example of LV myocardium clustering. Different grey values represent different clusters.

As a functionally significant stenosis is expected to have a local impact on the myocardial blood perfusion, and consequently on the texture characteristics of the contrast enhancement of hypoperfused regions, the LV myocardium is divided into a number of spatially connected clusters as described in step 606 of FIG. 6. Clustering is achieved, for instance, using the fast K-means algorithm ("*Web-scale k-means clustering*," Proceedings of the 19$^{th}$ international conference on World wide web, ACM, 2010, pp 1177-1178), based on the spatial location of the myocardial voxels. FIG. 9 shows the result is such a clustering method. Within a single cluster, a large deviation of an encoding likely indicates its inhomogeneity, and thereby the presence of an abnormal myocardial tissue. Therefore, the standard deviation (STD) of each of the encodings over all voxels within a cluster is calculated. Thereafter, to describe the whole LV myocardium rather than its clusters, the maxima of the standard deviations of each encoding over all clusters are used as features describing the LV myocardium of each patient. Furthermore, higher order statistical parameters can be calculated and used such as skewness, kurtosis, or higher moments. Besides the use of the STD to reduce the high dimensionality of the encodings over all the voxels within a cluster, alternative ways of compressing the local encodings can be performed. For instance, by means of restricted Boltz-mann machine (as for example presented by Bengio et al., "*Representation Learning: A Review and New Perspectives*," IEEE Trans. Pattern Anal. Mach. Intell. 35 (8), 2013, 1798-1828) or deep belief networks (as for example taught by Lee at al., "*Convolutional deep belief networks for scalable unsupervised learning of hierarchical representations*," Proceedings of the 26th Annual International Conference on Machine Learning, 2009, pp. 609-616). These generative approaches, which belong to the undirected graphical models, could be employed to represent a group of voxel encodings by more compressed but yet descriptive representations.

The clustering can be performed using any clustering method. Another example of clustering is by means of the American Heart Association 17-segment heart model (Cerqueira et al., "*Standardized myocardial segmentation and nomenclature for tomographic imaging of the heart. A statement for healthcare professionals from the Cardiac Imaging Committee of the Council on Clinical Cardiology of the American Heart Association*," Circulation Jan. 29, 2002; 105:539-542). The clustering can also be performed based on a patient specific 13-territory model, as taught by Cerci et al., "*Aligning Coronary Anatomy and Mycoardial Perfusion Territories: An Algorithm for the CORE320 Multicenter Study*," Circ Cardiovasc Imaging. 2012, 5:587-595. Finally, based on the extracted features, patients are classified into those with a functionally significant coronary artery stenosis or those without.

Figure 10:
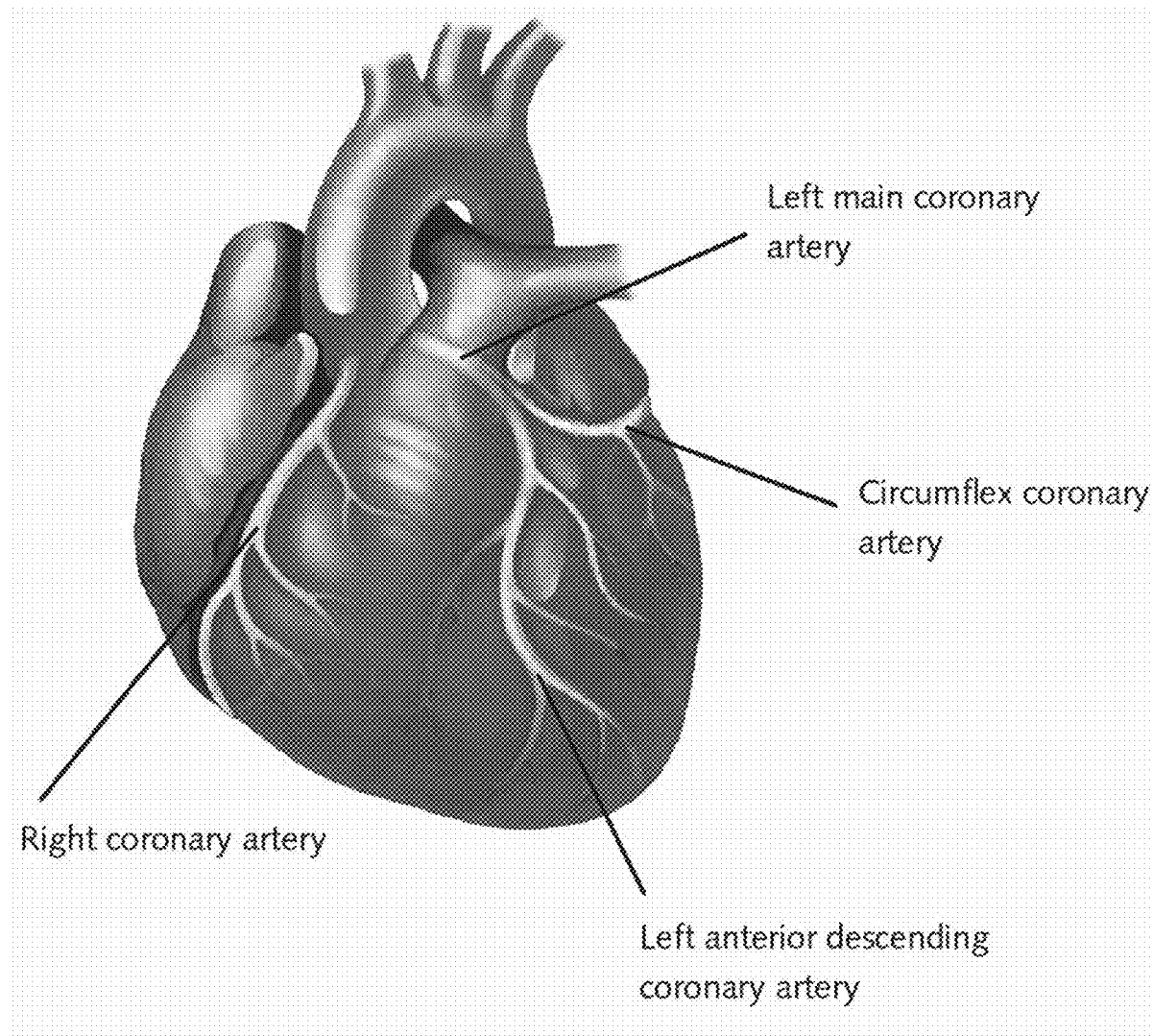
FIG. 10 shows an example of coronary anatomy.

With respect to clustering, coronary tree anatomy can be optionally used to improve clustering of features. Different parts of the myocardium are subtended by different sections of the coronary tree as can be seen in FIG. 10. When performing clustering of features it can occur that certain clusters contain voxels which receive their blood supply from the left side of the coronary tree (i.e. left anterior descending artery or circumflex artery) as well as voxels which receive their blood supply from the right side of the coronary tree (i.e. posterior descending artery). When a stenosis is, for instance, only present in the posterior descending artery of the coronary tree, this will affect the features of the voxels in the LV myocardium that are subtended by that section of the coronary tree. To avoid distortion of information within clusters, information regarding the coronary tree can be added to guide the clustering. The size of the cluster can for instance be limited to avoid territories supplied by more than one main coronary (e.g. left coronary artery, circumflex artery, and right coronary artery). Such a method to identify patient-specific blood supply territories may involve segmentation of the myocardium, for instance by methods discuss previously, and segmentation of the coronary tree centerline as for instance by Metz et al., "*Coronary centerline extraction from CT coronary angiographic images using a minimum cost path approach*," Med Phys. 2009 December; 36(12): 5568-79. Based on the patient specific segmented myocardium and the patient specific segmented coronary tree, patient-specific blood supply territories can be calculated for instance by the method as described by Zakkaroff et al., "*Patient-specific coronary blood supply territories for quantitative perfusion analysis*," Computer Methods in Biomechanics and Biomedical Engineering: Imaging & Visualization 2016 or by the method as taught by Termeer et al, "*Patient-Specific Mappings between Myocardial and Coronary Anatomy*," Scientific Visualization: Advanced Concepts, 2010, page 196-209 or by the method as taught by Nils Hampe et al., "*Graph attention networks for segment labeling in coronary artery trees*", Proc. SPIE 11596, Medical Imaging 2021: Image Processing, 1159611 (15 Feb. 2021); doi: 10.1117/12.2581219. Various segmentation and clustering methods may be utilized.

Within step 608 of FIG. 6, a feature vector is defined. For example, the feature vector may comprise a series of factors, where each of the factors has a value related to a characteristic of interest. For example, the factors may represent an amount of variation in the characteristic of interest over multiple clusters. The factors may correspond to separate encodings. For example, when 50 or more encodings are utilized, the feature vector may comprise a series of 50 or more factors. As one example, the characteristic of interest may represent grey scale of voxels or another characteristic acquired by a diagnostic imaging modality that concerns anatomical and/or functional aspects of the myocardium. The factor may represent a deviation (e.g., maximum or minimum standard deviation) in the characteristic of interest (e.g., grey scale) over all or a subset of the clusters defined during segmentation. An example of a feature vector is given hereafter, where the feature vector comprises a series of variation factors for N encodings and where the variation factors correspond to the maximum standard deviation of the encodings resulting from the CAE within each cluster as described before:

$$\text{Feature vector} = \begin{pmatrix} \text{Maximum } STD \text{ over all clusters for encoding } 1 \\ \text{Maximum } STD \text{ over all clusters for encoding } 2 \\ \ldots \\ \text{Maximum } STD \text{ over all clusters for encoding } N-1 \\ \text{Maximum } STD \text{ over all clusters for encoding } N \end{pmatrix}$$

In above example of a feature vector, 'the Maximum STD over all clusters for encoding i', where $i=1, \ldots N$, is obtained by first computing the standard deviations of a single encoding i over all voxels in a single cluster; and subsequently determining the maximum of all standard deviations of that encoding i over all clusters as described previously.

As another example, the factors may represent an intensity of the characteristic of interest over multiple segments of the myocardium. For example, when the 17 segment model as defined by the AHA is utilized, the feature vector may comprise a series of 17 factors. More specifically, the factors may represent a mean intensity of the characteristic of interest (e.g. grey scale) over all or a subset of the segments defined during segmentation. An example of a feature vector based on a feature engineered Gaussian operator in combination with the AHA 17-segment model is given by:

$$\text{Feature vector} = \begin{pmatrix} \text{Mean } G_{intensity} \text{ within } AHA \text{ segment } 1 \\ \text{Mean } G_{intensity} \text{ within } AHA \text{ segment } 2 \\ \ldots \\ \text{Mean } G_{intensity} \text{ within } AHA \text{ segment } 16 \\ \text{Mean } G_{intensity} \text{ within } AHA \text{ segment } 17 \end{pmatrix}$$

In the above example, $G_{intensity}$ is computed by a 2D or 3D Gaussian operator with a specific kernel size, for instance 3 voxels. Both examples above of feature vectors are based on local features in which dimensionality reduction is performed. Additionally or alternatively, the feature vector may incorporate global features, for instance myocardium volume and myocardium thickness. For example, the feature vector may include a series of factors having different types. For example, a subset of the factors in the series may represent mean intensity within segments, while another subset of the factors in the series represent values indicative of myocardium volume, minimum myocardium thickness and maximum myocardium thickness. The following example shows a feature vector having factors of different types:

$$\text{Feature vector} = \left\{ \begin{array}{l} \text{Mean } G_{intensity} \text{ within } AHA \text{ segment 1} \\ \text{Mean } G_{intensity} \text{ within } AHA \text{ segment 2} \\ \ldots \\ \text{Mean } G_{intensity} \text{ within } AHA \text{ segment 16} \\ \text{Mean } G_{intensity} \text{ within } AHA \text{ segment 17} \\ \text{Myocardium volume} \\ \text{Minimum myocardium thickness} \\ \text{Maximum myocardium thickness} \end{array} \right\}$$

In case the CCTA dataset comprises multiple phases within the cardiac cycle, the myocardial features extracted from each phase, by performing the steps described by 604, 605 and 606 of FIG. 6 for each phase separately, can be added to the feature vector. The same approach can be applied in case the CCTA dataset consists of a multi-energy CCTA dataset. It might be beneficial to resample the multiphase CCTA dataset in the temporal domain to a fixed amount of cardiac cycles. With this approach, variations in the temporal resolution between different multiphase CCTA datasets can be resolved. Alternatively, instead of adding each phase (or energy level) separately (by performing the steps described by 604, 605 and 606 of FIG. 6), a different deep learning network architecture can be deployed in which the multiple phases (or energy levels) are directly incorporated.

Besides the extracted features as described above (encodings and segments), also additional information represented by step 607 of FIG. 6, can be used to build up the feature vector. For example, demographic information such as weight, height, gender, etc. of the patient can be used as additional information for the patient classification by addition as features to the feature vector.

Figure 11A:
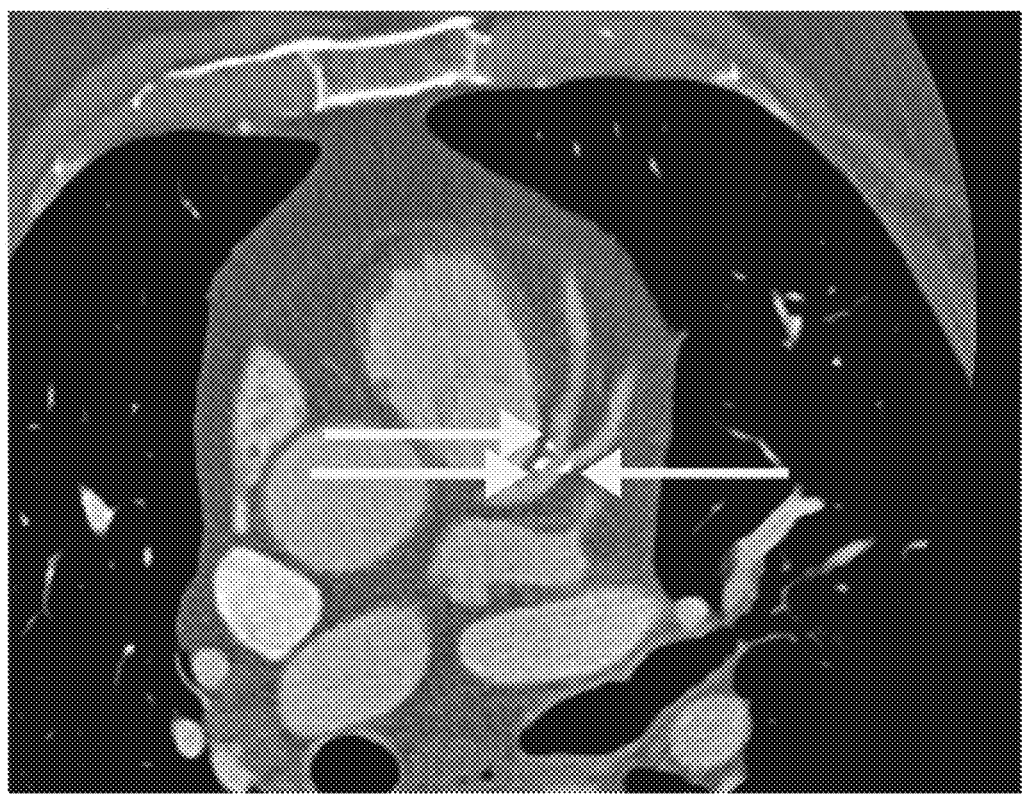
FIG. 11a shows an example of coronary calcium scoring. The white arrows identify coronary calcium within a CTTA dataset.
Figure 11B:
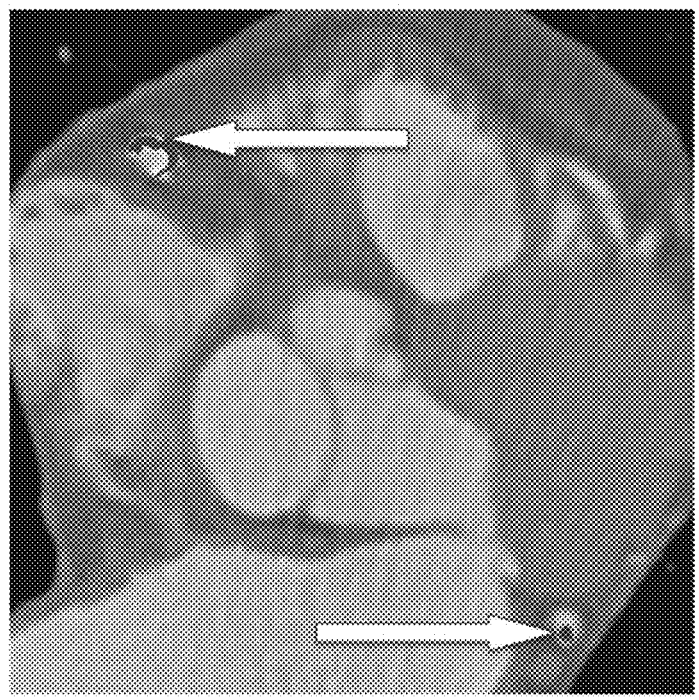
FIG. 11b shows an example of detection of coronary calcium scoring within a CCTA dataset. The white arrows point to the regions which are identified as coronary calcium.

The presence and amount of coronary artery calcification (see FIG. 11a) is a strong and independent predictor of cardiovascular events, which can be identified and quantified in CCTA as taught by Wolterink et al. "*Automatic Coronary Artery Calcium Scoring in Cardiac CT Angiography Using Paired Convolutional Neural Networks*," Medical Image Analysis, 2016. FIG. 11b, shows an example of detected coronary calcium within a CCTA dataset by using method as described by Wolterink et al. The feature vector can be expanded with information about the presence and extent of coronary calcium, per coronary artery (left anterior descending artery, right coronary artery, and circumflex) or the total coronary tree. Additional information can be incorporated characterizing coronary artery or other calcifications (e.g. in the aorta, heart valves, pericardium)

Coronary events are also associated with the total plaque burden, which includes coronary plaque which are not necessarily calcified. Beyond the detection of calcified plaque, CCTA has promise in characterizing the type of plaque (non-calcified and mixed) that is present. The total amount of plaque can be determined by (semi) automated method that detects the inner and outer coronary vessel walls as for instance taught by Dey et al., "*Automated 3-dimensional quantification of noncalcified and calcified coronary plaque from coronary CT angiography*," Cardiovasc Comput Tomogr. 2009, 3(6):372-382. The area between inner and outer vessel walls is counted as plaque. The feature vector can be expanded with the plaque burden as calculated by normalizing the volume of plaque within the vessel by the length of the vessel.

Additionally, an estimate of pressure drop, or pressure gradient, along a coronary vessel surrounding the myocardium of the heart can be incorporated into the feature vectors (e.g., the feature vectors of FIG. 6). Such an estimate of the pressure drop, or pressure gradient, along a coronary vessel surrounding the myocardium of the heart can be performed as disclosed by U.S. application Ser. No. 16/438,955 entitled "*Method and Apparatus for Quantitative Hemodynamic Flow Analysis*" to Bouwman et al. In summary, the method disclosed by U.S. application Ser. No. 16/438,955 calculates the pressure drop along a coronary vessel instantaneously by applying physical laws including viscous resistance and separation loss effects present in coronary flow behavior, as described by Gould et al. in "*Physiologic basis for assessing critical coronary stenosis. Instantaneous flow response and regional distribution during coronary hyperemia as measures of coronary flow reserve*", Am J Cardiol. 1974 January; 33(1):87-94 and Kirkeeide et al. in "*Assessment of coronary stenoses by myocardial perfusion imaging during pharmacologic coronary vasodilation. VII. Validation of coronary flow reserve as a single integrated functional measure of stenosis severity reflecting all its geometric dimensions*", J Am Coll Cardiol. 1986 January; 7(1):103-13. The pressure drop or pressure gradient can be based on the diameter or cross-section area of the inner coronary vessel wall of a coronary vessel surrounding the myocardium of the heart, which can be obtained from coronary artery analysis.

Figure 19:
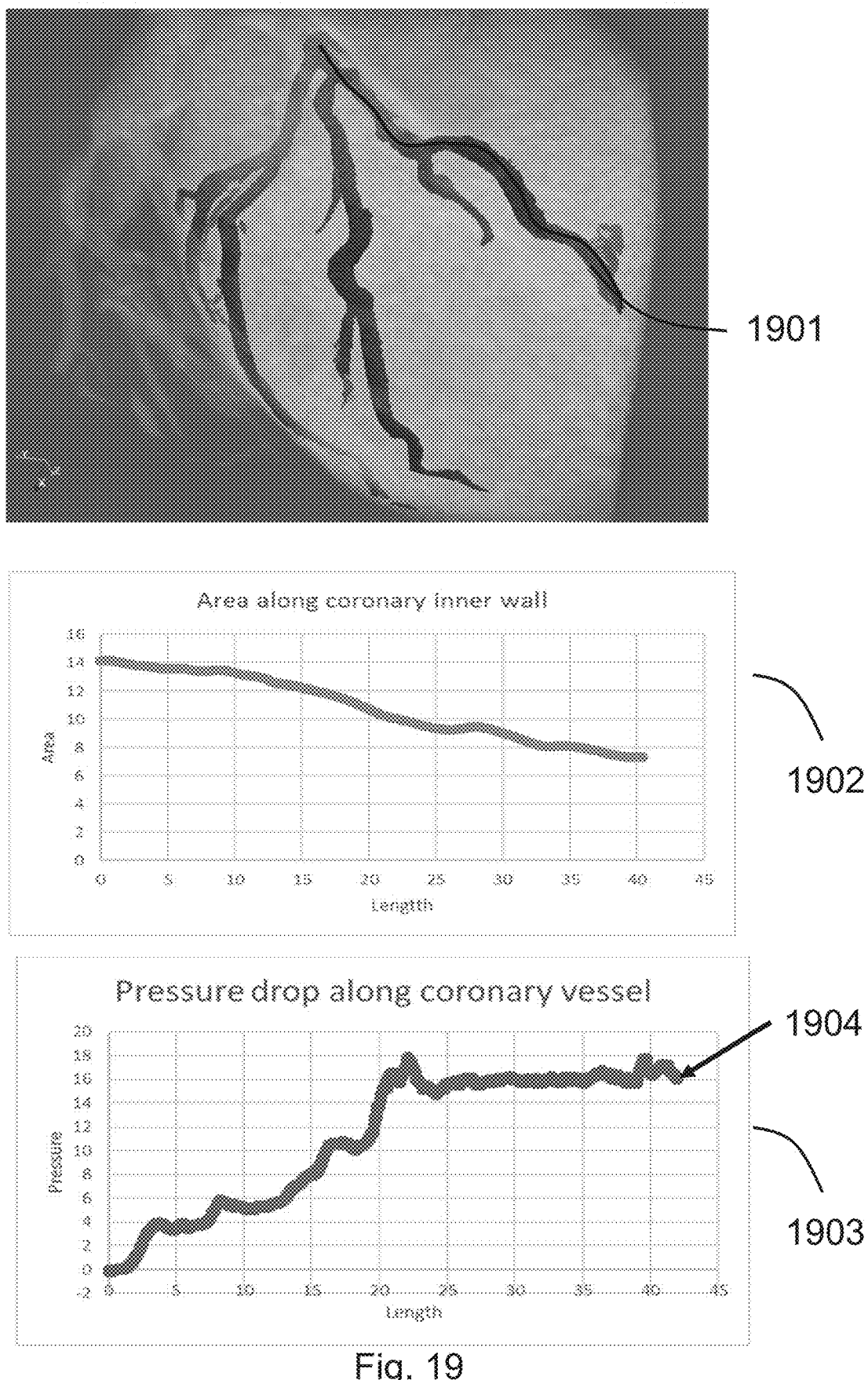
FIG. 19 shows the high-level method for determining the pressure drop along a coronary vessel.

FIG. 19 illustrates an exemplary method that estimates pressure drop, or pressure gradient, along a coronary vessel surrounding the myocardium of the heart, and incorporates data representing such pressure drop, or pressure gradient, into a feature vector (e.g., the feature vectors of FIG. 6). In 1901, coronary artery analysis can be used to obtain the inner coronary vessel wall of a coronary vessel surrounding the myocardium of the heart. For example, such coronary analysis can perform the method taught by Dey et al., "*Automated 3-dimensional quantification of noncalcified and calcified coronary plaque from coronary CT angiography*," Cardiovasc Comput Tomogr. 2009, 3(6):372-382, or as taught by Wolterink et al., "*Graph convolutional networks for coronary artery segmentation in cardiac CT angiography*", International Workshop on Graph Learning in Medical Imaging. Springer, Cham, 2019.

From the inner coronary vessel wall, geometrical features along the coronary vessel, such as a diameter or a cross-section area graph, can be extracted as shown by 1902.

Next, the diameter or cross-section area graph can be used to calculate an estimate of the pressure-drop, or pressure gradient along the coronary vessel length by the method as disclosed by U.S. application Ser. No. 16/438,955 and shown in 1903 or as disclosed by U.S. application Ser. No. 15/551,162.

The pressure-drop, or pressure gradient, along the coronary vessel can be used to calculate the value for a parameter representing fractional flow reserve (FFR) of the coronary vessel surrounding the myocardium of the heart or possibly some other hemodynamic index (or indices) of the coronary vessel surrounding the myocardium of the heart by the method as disclosed by U.S. application Ser. No. 16/438,955 For example, such hemodynamic index (indices) can relate to coronary flow reserve, instantaneous wave-free ratio, hyperemic myocardium perfusion, index of microcirculatory resistance or other hemodynamic parameter along the coronary vessel surrounding the myocardium of the heart.

Finally, data representing one or more hemodynamic parameters such an estimate of the pressure drop, or pressure gradient and/or other hemodynamic index (or indices) can be incorporated into the feature vectors. Such integration can be performed in several ways. For example, the feature vector can be extended with the most distal pressure drop value (1904) for one or more coronary vessels surrounding the myocardium of the heart.

In another example, the clusters (step 606) can be weighted with the calculated pressure drop along the coronary vessel surrounding the myocardium of the heart. This can be obtained by linking the spatial locations of the calculated pressure drop along the coronary vessel to the closest cluster corresponding to this location and then calculating a weight or weighting for this closest cluster according to the calculated pressure drop at the corresponding location. Alternatively, the size of the clusters can be defined according to the calculated pressure drops corresponding to the spatial locations of such calculated pressure drops.

Another example of additional information is protocol information. As described before, contrast material is administered to the patient prior to depiction of the heart and coronary arteries. Imaging is started once contrast medium density surpasses a predefined threshold by either visual inspection, or by determination of contrast medium density in a predefined anatomical structure. For instance, the threshold used to start the CCTA acquisition, the anatomical structure used to assess the threshold, type of CT scanner, moment within the cardiac cycle the CCTA acquisition is performed (trigger time), and or the contrast medium administered to the patient during acquisition can be used as additional information within the feature vector.

Additionally, if present, information obtained from any of the various forms of dual-energy, spectral, multi-energy or photon-counting CT scan can be used as an additional feature for the classification. In CT, materials having different compositions can be represented by identical pixel values on a CT image depending on the mass density of the material. Thus, the differentiation and classification of different tissue types and contrast agents can be challenging. In a Dual-energy scan two CT datasets are acquired with different x-ray spectra, allowing the differentiation of multiple materials. Not only anatomical information is present but also information related to tissue composition. Therefore, a better insight is available regarding the lumen and any ischemic tissue. Information regarding tissue composition extracted from any of the various forms of dual-energy, spectral, multi-energy or photon-counting CT scan (for instance the presence of ischemic tissue, or contrast material) can be used as an additional feature.

Blood flow distribution within the myocardium and the location and extent of areas at risk in case of coronary artery disease are dependent on the distribution and morphology of intramural microvascular (vascular crowns). The epicardial coronary arteries (right coronary artery, left coronary artery) distribute blood flow to different regions of the heart muscle through the myocardium microvasculature. The myocardium can be divided from epicardium to endocardium into three layers; subepicardial, mid-myocardium and subendocardial. The subendocardial layer is more vulnerable for ischemia and infarctions than the other layers as taught by van den Wijngaard J P et al., "*Model prediction of subendocardial perfusion of the coronary circulation in the presence of an epicardial coronary artery stenosis,*" Med Biol Eng Comput 2008, 46: 421-432. Optionally, this knowledge can be integrated in the feature vector calculation. For instance, the clusters (606) can be weighted with the spatial layer location, or a myocardium layer prediction model can be added to the feature vector. Such a myocardium layer prediction model can be pre-generated based on for instance physiological experiments as taught by van Horssen et al., "*Perfusion territories subtended by penetrating coronary arteries increase in size and decrease in number toward the subendocardium,*" Am J Physiol Heart Circ Physiol 2014, 306: H496-H504 or as taught by Nils Hampe et al., "*Graph attention networks for segment labeling in coronary artery trees*", Proc. SPIE 11596, Medical Imaging 2021: Image Processing, 1159611 (15 Feb. 2021); doi: 10.1117/12.2581219.

Figure 12:
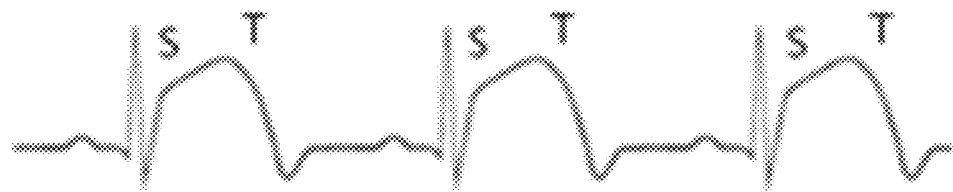
FIG. 12 shows an example of a normal ECG and an ECG with an elevated ST segment.
Figure 12:
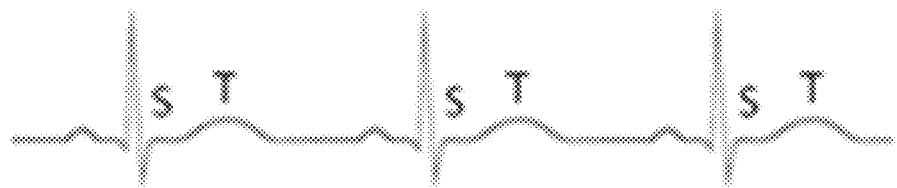

When an Electro Cardio Gram (ECG) is available from the patient, its characteristics can be used as additional information. An ECG is a representation of the electrical activity in the heart muscle. The ECG registers the electric stimulus that causes the heart muscle cells to contract. This stimulus travels from one muscle cell to the other. The cardiac conduction system ensures that this is done in the right sequence (i.e. atrium then ventricles). Typically, an ECG comprises of four segments, a P wave, a QRS complex, a T wave and a U wave. The P wave represents atrial depolarization, the QRS complex represents ventricular depolarization, the T wave represents ventricular repolarization and the U wave represents papillary muscle repolarization. Changes in the structure of the heart and its surroundings (including blood composition) change the patterns of these four segments. For instance, a heart attack or myocardial infarction is visible in the ECG by an elevation of the ST segment as can be seen in FIG. 12. This is due to the fact that a section of the myocardium is ischemic due to the heart attack. But also for instance chest pain (angina pectoris) and a heart block have ischemic markers that a recognizable on an ECG. When translating the 12-lead ECG into a vectorcardiogram for instance as taught by Engels et al., "*The synthesized vectorcardiogram resembles the measured vectorcardiogram in patients with dyssynchronous heart failure,*" J Electrocardiol; 48(4):586-592, the electrical activity, as a vector, can be assessed in the three principal directions. This allows more accurate and more robust extracted of electrical parameters (Edenbrandt et al., "*Vectorcardiogram synthesized from a 12-lead ECG: Superiority of the inverse Dower matrix,*" Journal of Electrocardiology, December 1988, 21(4):361-7). For example, myocardial infarction and right ventricular hypertrophy assessed with synthesized vectorcardiogram are superior to the corresponding 12-lead ECG criteria. Parameters extracted from synthesized vectorcardiogram are for instance QRS loop perimeter, QRS vector difference, area under the QRS complex, ST segment and T-wave in the (X, Y, Z) leads; ST-T vector magnitude difference, T-wave vector magnitude difference, and the spatial angle between the QRS complex and the T-wave.

Other important feature which can be used as additional information are cardiac biomarkers. When blood is taken from the patient, levels of cardiac biomarkers in the blood can be examined. These markers include enzymes, hormones, and proteins. Cardiac biomarkers show up in the patient's blood after their heart has been under severe stress due to ischemia, for instance due to a heart attack. The levels of the biomarkers can be used to determine the size of the heart attack and how serious the effect of the heart attack is. Cardiac biomarkers are for instance cardiac troponin and creatine kinase.

Furthermore, information regarding the presence of fat (adipose tissue) surrounding the heart or inside the heart, can be used as additional information. This information can for instance be obtained using MR or CT data. Fat present directly around the heart (pericardial fat) may predict narrowed arteries. People with fat in the area around the heart and under the breastbone in the chest, where it sits in close proximity to the heart, may face a higher risk of heart disease compared to people who store fat in other areas. This is due to the fact that fatty tissue releases inflammatory chemicals that may speed the development of atherosclerosis.

Figure 13:
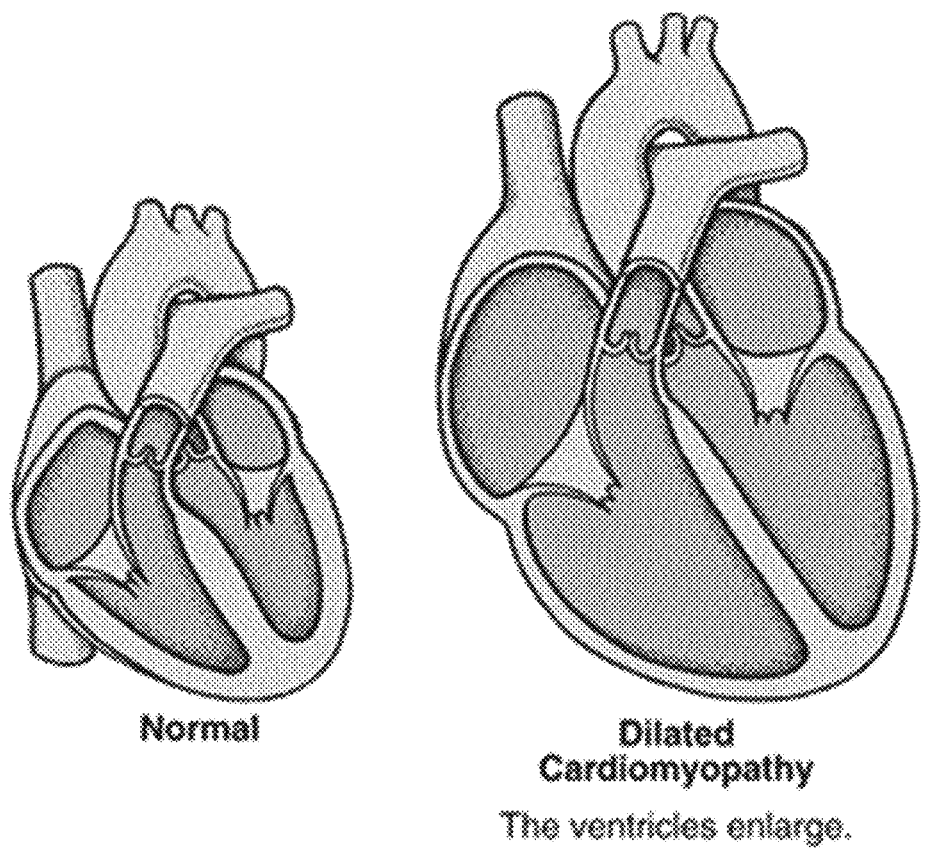
FIG. 13 shows an example of dilated cardiomyopathy.

Another feature that can be used is the shape of the myocardium. For instance, the presence of dilated cardiomyopathy (DCM). DCM is a condition in which the heart becomes enlarged and cannot pump blood efficiently. DCM can be due to replacement of normal myocardium by deposition of fibrous tissue in the myocardium, for instance subsequent to a previous myocardial infarction, or other diseases. An example of DCM can be seen in FIG. 13. Information on the shape of the myocardium and/or shape of the cardiac chambers can be obtained by principal component analysis (PCA). PCA is a dimension-reduction method that can be used to reduce a large set of variables to a small set that still contains most of the information in the large set, it is a mathematical procedure that transforms a number of (possibly) correlated variables into a (smaller) number of uncorrelated variables called principal components. The first principal component accounts for as much of the variability in the data as possible, and each succeeding component accounts for as much of the remaining variability as possible and each succeeding component in turn has the highest variance possible under the constraint that it is orthogonal to the preceding components. An example of computing ventricular shape parameters by PCA is provided by Medrano-Gracia et al., "*Left ventricular shape variation in asymptomatic populations: the Multi-Ethnic Study of Atherosclerosis,*" J Cardiovasc Magn Reson. 2014 Jul. 30; 16:56. In this work Medrano-Gracia and coworkers sought to establish the most important components of left ventricle shape and function present in an examined cohort. For current application, the reference standard (601) database can be used to define the principal components for the LV, RV and/or atriums by means of PCA. For this the desired cardiac structures needs to be segmented (only one time) for the dataset used to define the principal components for that cardiac structure. For this the method as described by step 302 of FIG. 3 can be used, or any other method. Next the variation of the principal components extracted from the examined CCTA dataset can be computed and added as a feature to the feature vector. Alternatively, the segmentation within step 302 of FIG. 3 can be performed by active shape model segmentation algorithms in which PCA is incorporated, or any other segmentation algorithm in which PCA is incorporated. By using such an algorithm the principle components of the examined CCTA dataset are automatically defined within this segmentation approach as for instance taught by van Assen et al., "*3D Active Shape Model Matching for Left Ventricle Segmentation in cardiac CT,*" Phytochemistry January 2003, 5032, or by D. Fritz et al., "*Segmentation of the left and right cardiac ventricle using a combined bi-temporal statistical model,*" Proceedings of SPIE—The International Society for Optical Engineering, March 2006, 6141, DOI10.1117/12.652991. Another feature based on PCA can be the myocardial tissue stiffness as taught by Wang et al., "*Principal component analysis used to derive patient-specific load-free geometry and estimate myocardial stiffness in the heart,*" 5th International Conference on Computational and Mathematical Biomedical Engineering-CMBE2017. Another feature that can be used is myocardial strain. Myocardial strain is a method for measuring regional or global deformation of the myocardium and can be used in the assessment of conditions that impair myocardial function including ischemic heart disease, hypertensive heart disease, dilated cardiomyopathy, hypertrophic cardiomyopathy, myocarditis, and infiltrative cardiomyopathies, cardiac dyssynchrony. Strain abnormalities develop in most settings before overt clinical disease or even mild subclinical abnormalities of ventricular ejection fraction and have prognostic significance, as do severity and progression of strain abnormalities in advanced or treated disease. Myocardium strain can be added to the feature vector for instance by the method as though by Wong et al., "*Myocardial strain estimation from CT: towards computer-aided diagnosis on infarction identification,*" SPIE Medical Imaging conference, March 2015, DOI 10.1117/12.2081464.

Other features that can be used are end diastolic LV blood volume, end systolic LV blood volume, ejection fraction, cardiac output, diameter of ascending aortic, present of bicuspid aortic valve, cardiac valve insufficiency (mitral, aorta, tricuspid and/or pulmonary) and/or the coronary tree dominance; left dominant, right dominant, balanced, or small right/left dominant.

In additional to all the features regarding the LV myocardium also the same information regarding the RV myocardium can be taken into account for the classification.

An example of a feature vector (step 608 of FIG. 6), considering the maximum standard deviation within each cluster as described before, and taking some of the additional features into considerations, is given by:

$$\text{Feature vector} = \begin{Bmatrix} \text{Maximum } STD \text{ over all clusters for encoding } 1 \\ \text{Maximum } STD \text{ over all clusters for encoding } 2 \\ \ldots \\ \text{Maximum } STD \text{ over all clusters for encoding } N-1 \\ \text{Maximum } STD \text{ over all clusters for encoding } N \\ \text{Total coronary calcium} \\ \text{Number of calcified lesions} \\ \text{Patient blood pressure} \\ \text{Patient age} \\ \text{Amount of creatine kinase} \\ \text{Coronary plaque burden} \end{Bmatrix}$$

Extracted features and features obtained from additional information that are present that can be used to classify a patient as having functionally significant stenosis or not.

Figure 14:
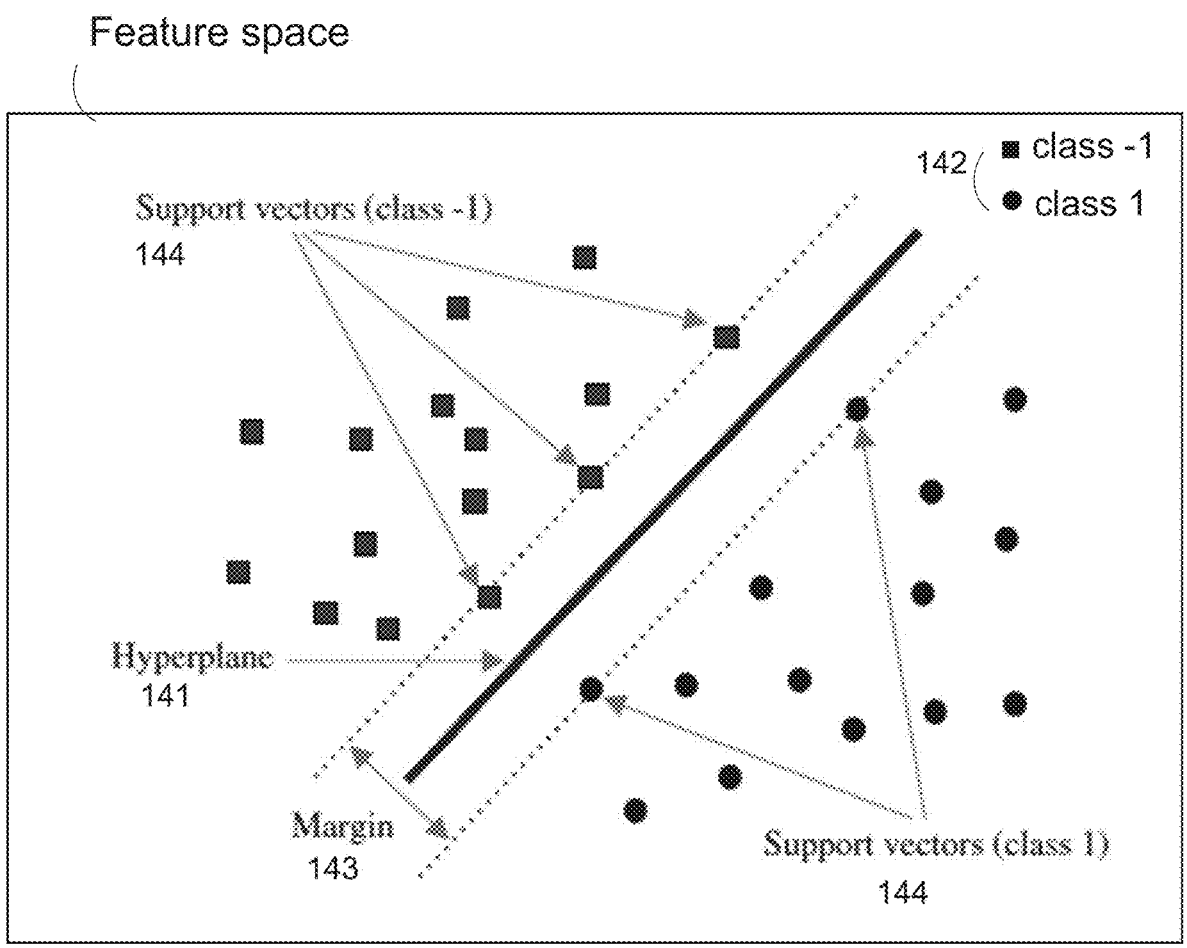
FIG. 14 shows an example of a feature space wherein the training data is represented as points, mapped so that the data of the separate categories are divided by a clear gap that is as wide as possible.

At step 609 of FIG. 6 the feature-perfusion classification model is learned by means of a supervised classifier. Several supervised classifiers could be used, for instance, a support vector machine (SVM) classifier. A SVM is a supervised machine learning classifier that can be employed for both classification and regression purposes. SVMs are based on the idea of finding a hyperplane (141, FIG. 14) that best divides a dataset into predefined classes (142, FIG. 14). As a simple example, for a classification task with only two features is illustrated in FIG. 14. During training of the SVM, a hyperplane that best separates samples of two classes is found by maximizing the margin around the decision boundary while minimizing the number of training samples within the margin (FIG. 14). The margin (143, FIG. 14) is determined by the support vectors (144, FIG. 14) i.e. training samples that lie on the margin. Intuitively, a good separation is achieved by the hyperplane that has the largest distance to the nearest training-data point of any class. In other words, the distance between the hyperplane and the nearest support vector from either set is known as the margin. The goal of SVM is to find a hyperplane with the greatest possible margin between the hyperplane and any point (support vector) within the training set.

Other kinds of classifiers may include neural networks, Bayesian classifiers, Tree Ensembles (e.g., random Forests) (Kotsiantis et al, "*Supervised Machine Learning: A Review of Classification Techniques,*" Informatica 31, 2007, 249-268).

To be able to use a supervised (SVM) classifier, reference data must be present that can be used as a reference standard. The reference standard is a database from multiple patients (step 601). Each set within this database contains a) contrast enhanced CT datasets (step 602) with belonging b) reference value (step 603).

In a preferred embodiment, the reference value (603), representing a fluidodynamic parameter, is an invasive fractional flow reserve (FFR) measurement as performed during X-ray angiography which belongs to the contrast enhanced CT dataset (602). For example, FFR is measured with a coronary pressure guidewire at maximal hyperemia induced by intravenous adenosine. During X-ray angiography the FFR wire is placed as distally as possible in the target vessel and FFR is assessed by means of a manual or automatic pullback in the distal part of the target vessel. Finally, the FFR wire is retrieved at the level of the guiding catheter to achieve a FFR value of 1.00 in order to assess the quality of the measurement performed. When multiple FFR measurements are available due to repeated measurements or multiple stenosis, the minimal value is taken as the standard of reference. The reference value (603) can be any parameter which links the patient specific CCTA datasets to myocardial ischemia of that patient. For instance, the reference value (603) can be the measured coronary flow reserve or the index of microcirculatory resistance which provides a measurement of the minimum achievable microcirculatory resistance in a target coronary artery territory, enabling a quantitative assessment of the microvascular integrity. Other examples of different parameters for the reference value (603) are the occurrence of major adverse cardiac events (MACE) within a predefined amount of time after acquisition of the CCTA dataset, or if the patient underwent revascularization within a predefined amount of time after acquisition of the CCTA dataset, or the results of cardiac stress test, the results of myocardial magnetic resonance imaging (MM) perfusion, SPECT, PET, CT perfusion, or ultrasound.

Using a database of reference values (603), which corresponds to the used CCTA dataset (602), each reference value (603) is marked as belonging to one of two classes, for instance "functionally significant stenosis present" (invasive FFR<for instance 0.8) or "no significant stenosis present" (invasive FFR>for instance 0.8) (the known labels), the SVM classifier learns to separate the different classes. First, each training sample (e.g. CCTA dataset) is represented as a point in an n-dimensional feature space, where n is the number of computed features (e.g. the number of features in the feature vector, the result of step 608 of FIG. 6). For all reaming CCTA cases in the database (602), such a feature vector is computed. All training samples (e.g. CCTA cases in the database) are used to train the chosen classifier. In the training phase, the SVM classifier finds the hyperplane that makes the best separation between the classes i.e. by finding a hyperplane separating two classes with the largest margin as illustrated in FIG. 14.

SVM is in nature a two-class classifier. Nevertheless, multi-class classification, i.e. classification in multiple classes, can be performed by e.g. performing multiple 2-class classifications (e.g. chosen class vs. all remaining classes or between every pair of classes—one vs one). Hence, the feature-perfusion classification model can be trained to recognize multiple classes, for example "no functionally significant stenosis present", "mild functionally significant stenosis present" or "severe functionally significant stenosis present", or any categories chosen based on the reference value (step 603 of FIG. 6). When the reference value (FIG. 6, 603) is an invasive FFR measurement, above classification can be achieved using for instance the following invasive FFR threshold values:

Invasive FFR>0.9, "no functionally significant stenosis present"
Invasive FFR between 0.7 and 0,8 "mild functionally significant stenosis present"
Invasive FFR<0.7, "severe functionally significant stenosis present"

Figure 15:
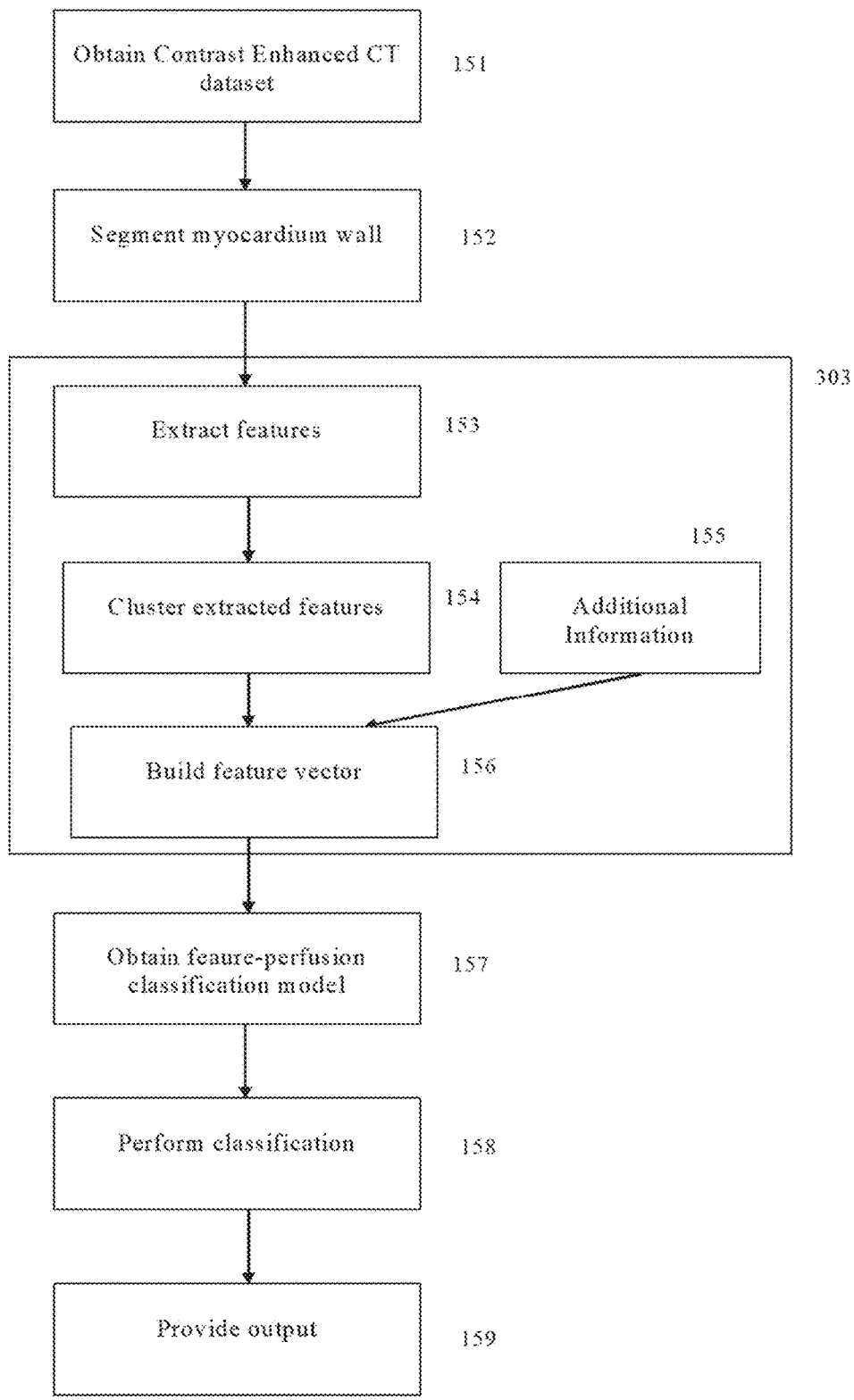
FIG. 15 shows a flowchart of an embodiment of the present application for the prediction phase.

Once the system is trained, new unseen CCTA datasets are classified into the classes as defined during the training phase, which is further explained by the flowchart of FIG. 15.

FIG. 15 illustrates a framework for implementing the prediction phase, to classify the severity of vessel obstruction(s) within unseen CCTA datasets; to determine the presents of functional significant stenosis in one or more coronary arteries from a CCTA dataset. The unseen CCTA dataset is represented by block 151 of FIG. 15.

In block 152 the myocardium segmentation takes place, according to one of the methods as described previously by block 302 of FIG. 3.

Figure 16:
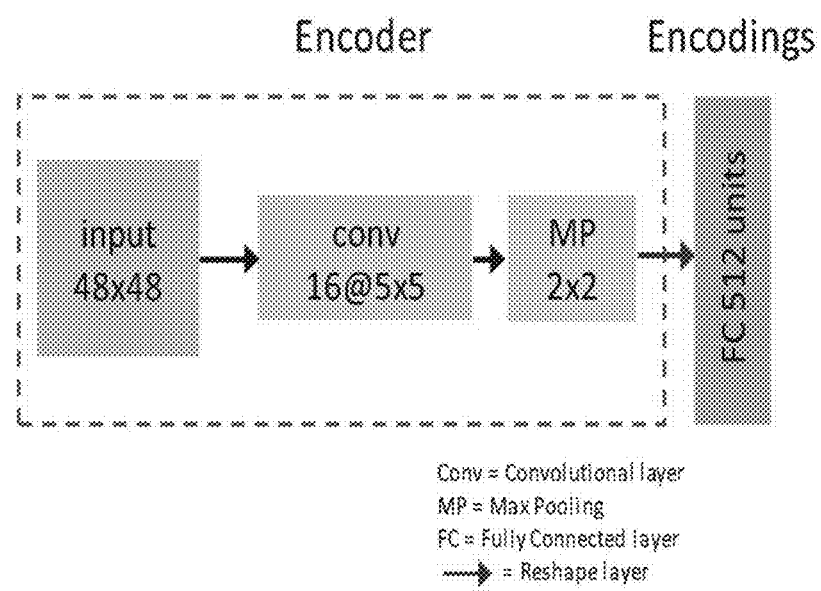
FIG. 16 shows an example of the architecture of a convolution auto encoder (CAE), as used during the prediction phase.

Within block 303 of FIG. 15 the computing of the features takes place, and is identical as described previously for block 303 of FIG. 6. Block 153 of FIG. 15 describes the feature extraction and is identical to the method as described by step 605 of FIG. 6. In a preferred embodiment, the feature extraction during the learning phase, as performed by block 303 of FIG. 6, is performed by means of CAE. Within the prediction phase the architecture of the CAE is slightly different. As describe before in block 605 and referring to FIG. 6, after the CAE is trained, the decoder part can be removed, and the fully connected layer becomes the output layer which is used to generate encodings for unseen patches. An example of such CAE architecture as used in the prediction phase is presented in FIG. 16. This figure shows the CAE architecture for the prediction phase for the example as presented by FIG. 7. Step 154 within FIG. 15 describes the clustering and is identical to the method as described in step 606 of FIG. 6. Block 155 describes the additional information and is identical to the methods as described in step 607 of FIG. 6. Next the feature vector is generated within step 156 by the same method as performed during the learning as describe previously by block 608 of FIG. 6. In case additional information was used in the learning phase, the same methods are performed within step 175 during the prediction phase.

Step 157 of FIG. 15 represents the feature-perfusion classification model as learned during the learning phase as described by step 609 of FIG. 6.

Figure 17:
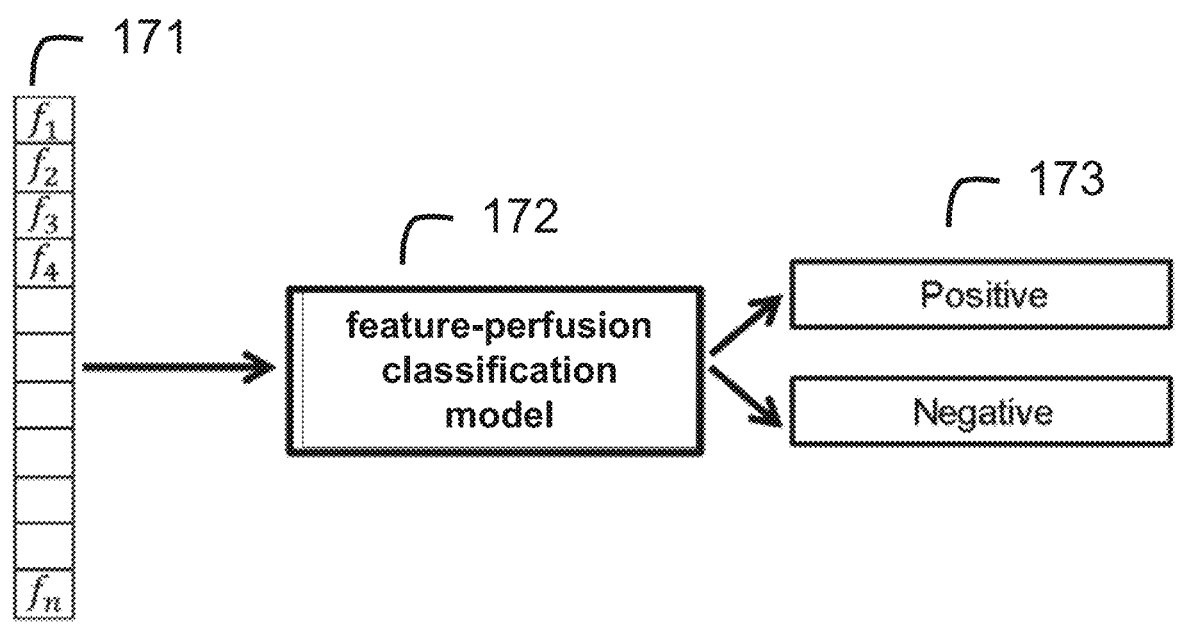
FIG. 17 shows an illustration of the classifier to classify unseen data. Within this visual representation, the input is the feature vector computed from the unseen image and the output two classes.

Finally, in step 158, the classifier assigns new unseen CCTA datasets into the categories as defined during the training phase. This classifier is the same classifier as used in block 609 in FIG. 6. Within the prediction phase, unseen CCTA dataset are mapped by step 158 of FIG. 15 in the n-dimensional feature space and its location in this feature space with respect to the hyperplane determines its class label. This classification results in an assessment of the severity that one or more coronary obstructions impedes oxygen delivery to the heart muscle and is represented by step 159 of FIG. 15. FIG. 17 shows a visual representation of the classifier. The result of step 156 of FIG. 15, representing the feature vector of the unseen image, is the input (171) of the classifier. Label 172 of FIG. 17 represents the feature-perfusion classification model (FIG. 15, 156), as learned during the learning phase as described by step 609 of FIG. 6. Label 173 of FIG. 17 represent the output of the classifier (FIG. 16, 159) incase two classes are learned; positive meaning one or more functionally significant coronary lesions present, and negative meaning no functionally significant coronary lesion present.

In case when dealing with multiphase CCTA datasets or multi energy CCTA datasets by the approach as described within step 608 of FIG. 6, the feature vector can be expanded with features from each phase or energy level. In this case, multiple feature-perfusion models can be learned for each of these sets (which, for example, can be single phase CCTA datasets, multiphase CCTA datasets, multi energy CCTA datasets). This means that during the training phase (FIG. 6) as well as during the prediction phase (FIG. 15), the feature-perfusion model of that particular CCTA dataset needs to be selected. This can be done for instance by examination of the information obtained through the "headers" of the DICOM file format. Also, multiple feature-perfusion models can be generated depended on the amount of additional information as described in step 607 of FIG. 6 (e.g. shape parameters, ECG parameters, etc.), meaning that in cases where not all additional features are available, the correct feature-perfusion model can be selected from the multiple models.

The present disclosure mainly describes the organ of interest as the myocardium and the vessels being the coronary arteries. The skilled person would appreciate that this teaching can be equally extended to other organs. For instance, the organ of interest can be the kidney, which is perfused by the renal arteries, or (parts) of the brain as perfused by the intracranial arteries. Furthermore, the present disclosure refers to CCTA datasets (in several forms). The skilled person would appreciate that this teaching can be equally extended to other imaging modalities, for instance rotational angiography, MRI, SPECT, PET, Ultrasound, X-ray, or the like.

Figure 18:
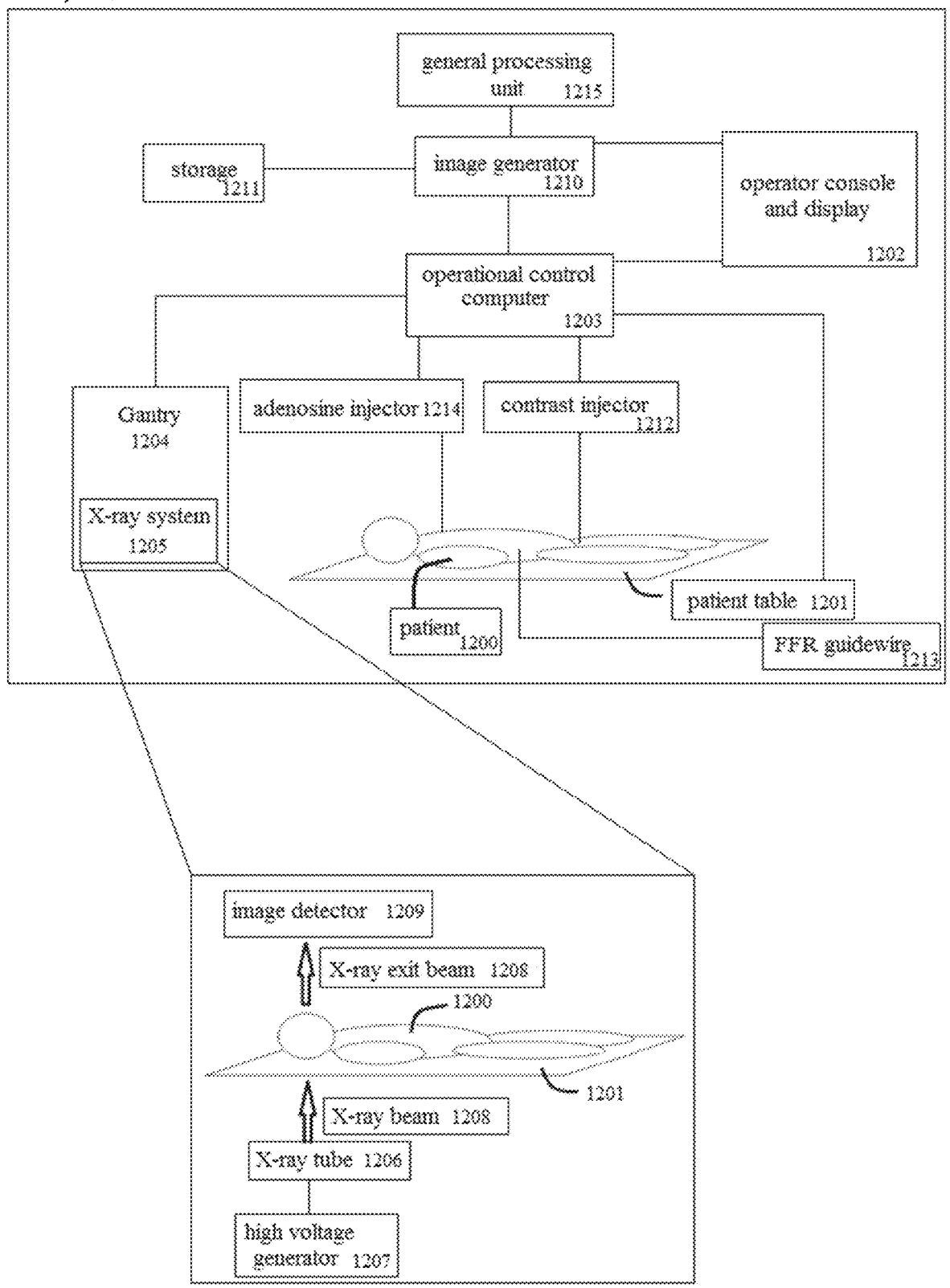
FIG. 18 shows a high-level block diagram of an example of a CT system.

The embodiment of this disclosure can be used on a standalone system or included directly in, for instance, a computed tomography (CT) system. FIG. 18 illustrates an example of a high-level block diagram of a computed tomography (CT) system. In this block diagram the embodiment is included as an example how the present embodiment could integrate in such a system.

The invention has been mainly disclosed with reference to the organ being the myocardium and the vessels being the coronary arteries. The skilled person would appreciate that this teaching can be equally extended to other organs. For instance the kidney, which is perfused by the renal arteries, or (parts) of the brain as perfused by the intracranial arteries. Furthermore, the invention has been mainly disclosed with reference to CCTA datasets (in several forms). The skilled person would appreciate that this teaching can be equally extended to other imaging modalities, for instance rotational angiography, MRI, SPECT, PET, Ultrasound, X-ray, or the like.

Portions of the system (as defined by various functional blocks) may be implemented with dedicated hardware, analog and/or digital circuitry, and/or one or more processors operating program instructions stored in memory.

The most common form of computed tomography is X-ray CT, but many other types of CT exist, such as dual-energy, spectral, multi-energy, or photon-counting CT. Also, positron emission tomography (PET) and single-photon emission computed tomography (SPECT) or combined with any previous form of CT.

The CT system of FIG. 18 describes an X-ray CT system. In an X-ray CT system an X-ray system moves around a patient in a gantry and obtains images. Through use of digital processing a three-dimensional image is constructed from a large series of two-dimensional angiographic images taken around a single axis of rotation.

For a typical X-ray CT system 120 an operator positions a patient 1200 on the patient table 1201 and provides input for the scan using an operating console 1202. The operating console 1202 typically comprises of a computer, a keyboard/foot paddle/touchscreen and one or multiple monitors.

An operational control computer 1203 uses the operator console input to instruct the gantry 1204 to rotate but also sends instructions to the patient table 1201 and the X-ray system 1205 to perform a scan.

Using a selected scanning protocol selected in the operator console 1202, the operational control computer 1203 sends a series of commands to the gantry 1204, the patient table 1201 and the X-ray system 1205. The gantry 1204 then reaches and maintains a constant rotational speed during the entire scan. The patient table 1201 reaches the desired starting location and maintains a constant speed during the entire scan process.

The X-ray system 1205 includes an X-ray tube 1206 with a high voltage generator 1207 that generates an X-ray beam 1208.

The high voltage generator 1207 controls and delivers power to the X-ray tube 1206. The high voltage generator 1207 applies a high voltage across the vacuum gap between the cathode and the rotating anode of the X-ray tube 1206.

Due to the voltage applied to the X-ray tube 1206, electron transfer occurs from the cathode to the anode of the X-ray tube 1206 resulting in X-ray photon generating effect also called Bremsstrahlung. The generated photons form an X-ray beam 1208 directed to the image detector 1209.

An X-ray beam 1208 comprises of photons with a spectrum of energies that range up to a maximum determined by among others the voltage and current submitted to the X-ray tube 1206.

The X-ray beam 1208 then passes through the patient 1200 that lies on a moving table 1201. The X-ray photons of the X-ray beam 1208 penetrate the tissue of the patient to a varying degree. Different structures in the patient 1200 absorb different fractions of the radiation, modulating the beam intensity.

The modulated X-ray beam 1208' that exits from the patient 1200 is detected by the image detector 1209 that is located opposite of the X-ray tube.

This image detector 1209 can either be an indirect or a direct detection system.

In case of an indirect detection system, the image detector 1209 comprises of a vacuum tube (the X-ray image intensifier) that converts the X-ray exit beam 1208' into an amplified visible light image. This amplified visible light image is then transmitted to a visible light image receptor such as a digital video camera for image display and recording. This results in a digital image signal.

In case of a direct detection system, the image detector 1209 comprises of a flat panel detector. The flat panel detector directly converts the X-ray exit beam 1208' into a digital image signal.

The digital image signal resulting from the image detector 1209 is passed to the image generator 1210 for processing. Typically, the image generation system contains high-speed computers and digital signal processing chips. The acquired data are preprocessed and enhanced before they are sent to the display device 1202 for operator viewing and to the data storage device 1211 for archiving.

In the gantry the X-ray system is positioned in such a manner that the patient 1200 and the moving table 1201 lie between the X-ray tube 1206 and the image detector 1209.

In contrast enhanced CT scans, the injection of contrast agent must be synchronized with the scan. The contrast injector 1212 is controlled by the operational control computer 1203.

For FFR measurements, an FFR guidewire 1213 is present, also adenosine is injected by an injector 1214 into the patient to induce a state of maximal hyperemia.

An embodiment of the present application is implemented by the X-ray CT system 120 of FIG. 18 as follows. A clinician or other user acquires a CT scan of a patient 1200 by selecting a scanning protocol using the operator console 1202. The patient 1200 lies on the adjustable table 1201 that moves at a continuous speed during the entire scan controlled by the operational control computer 1203. The gantry 1204 maintains a constant rotational speed during the entire scan.

Multiple two-dimensional X-ray images are then generated using the high voltage generator 1207, the X-ray tube 1206, the image detector 1209 and the digital image generator 1210 as described above. This image is then stored on the hard drive 1211. Using these X-ray images, a three-dimensional image is constructed by the image generator 1210.

The general processing unit 1215 uses the three-dimensional image to perform the classification as described above.

There have been described and illustrated herein several embodiments of a method and apparatus for automatically identify patients with functionally significant stenosis, based on the information extracted from a single CCTA image only.

While particular embodiments of the present application have been described, it is not intended that the present application be limited thereto, as it is intended that the present application be as broad in scope as the art will allow and that the specification be read likewise.

For example, multi-phase CCTA datasets can be used, functional assessment of renal arteries in relation to the perfused kidney can be assess based on the methodology disclosed, the data processing operations can be performed offline on images stored in digital storage, such as a PACS or VNA in DICOM (Digital Imaging and Communications in Medicine) format commonly used in the medical imaging arts. It will therefore be appreciated by those skilled in the art that yet other modifications could be made to the provided application without deviating from its spirit and scope as claimed.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art.

Similarly, any necessary files for performing the functions attributed to the computers, servers or other network devices may be stored locally and/or remotely, as appropriate.

Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer, or speaker). Such a system may also include one or more storage devices, such as disk drives, optical storage devices and solid-state storage devices such as random-access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above.

The computer-readable storage media reader can be connected with, or configured to receive, a computer-readable storage medium, representing remote, local, fixed and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or web browser.

It should be appreciated that alternate embodiments may have numerous variations from that described above. For example, customized hardware might also be used and/or particular elements might be implemented in hardware, software (including portable software, such as applets) or both.

Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the present application as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the present application to the specific form or forms disclosed, but on the contrary, the intention is to cover all modifications, alternative constructions and equivalents falling within the spirit and scope of the present application, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open ended terms (i.e., meaning "including, but not limited to,") unless otherwise noted. The term "connected," when unmodified and referring to physical connections, is to be construed as partly or wholly contained within, attached to or joined together, even if there is something intervening.

Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members.

Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the present application. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein.

Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. A method for assessing a severity of vessel obstruction, comprising:
    a) obtaining a contrast enhanced volume image dataset for a heart;
    b) segmenting a myocardium of the heart from the contrast enhanced volume data set of a);
    c) determining at least one geometrical feature of an inner vessel wall of at least one blood vessel surrounding the myocardium of the heart;
    d) determining a value of at least one hemodynamic parameter based on the at least one geometrical feature of c);
    e) defining data segments characterizing the myocardium of the heart of b);
    f) generating feature vectors related to the data segments of e), wherein the feature vectors include the at least one hemodynamic parameter of d);
    g) classifying the data segments of e) based on the feature vectors of f) and a classification model; and
    h) providing, as an output, a prediction indicative of a severity of vessel obstruction based on the classifying of g);
    wherein the classifying of g) uses a machine learning system to classify the feature vectors of f), wherein the machine learning system is trained from a database of contrast enhanced volume image data sets and associated training feature vectors extracted from the contrast enhanced volume image data sets.

2. The method of claim 1, wherein:
    the feature vectors of f) are generated by inputting patches of myocardial voxels to an additional machine learning system that generates data encodings that characterize the myocardium of the heart, and applying an automated clustering method to the data encodings.

3. The method of claim 2, wherein:
    the additional machine learning system uses at least one of: a convolutional auto-encoder, Gaussian filters, transmural perfusion ratio, Haralick features, myocardium thickness, myocardium volume, ventricular volume and organ shape.

4. The method of claim 2, wherein:
    the automated clustering method is based on voxels representing coronary tree anatomy.

5. The method of claim 1, wherein:
    the machine learning system represents a relationship between the training feature vectors and at least one reference parameter, wherein the at least one reference parameter is selected from the group consisting of i) an invasive fractional flow reserve measurement, ii) an index of microcirculatory resistance, iii) a coronary flow reserve measurement, iv) occurrence of major adverse cardiac events (MACE) within a predefined amount of time after acquisition of the contrast enhanced volume image dataset, v) occurrence of revascularization within a predefined amount of time after acquisition of the contrast enhanced volume image dataset, vi) the results of a cardiac stress test, and vii) the results of myocardial magnetic resonance imaging (MRI) perfusion, SPECT, PET, CT perfusion, or ultrasound.

6. The method of claim 1, wherein:
    the machine learning system is based on a supervised machine learning algorithm.

7. The method of claim 6, wherein:
the supervised machine learning algorithm is selected from the group consisting of a support vector machine, a neural network, a Bayesian classifier, and a Tree Ensemble.

8. The method of claim 1, wherein:
the feature vectors of f) include data indicative of an amount of perfusion experienced by the myocardium of the heart.

9. The method of claim 1, wherein:
the feature vectors of f) include additional information based on a patient ECG signal.

10. The method of claim 1, wherein:
the at least one geometrical feature of c) represents a diameter or cross-section area of the inner vessel wall.

11. The method of claim 1, wherein:
the at least one hemodynamic parameter of d) represents a pressure-drop or pressure gradient of a coronary vessel surrounding the myocardium.

12. The method of claim 1, wherein:
the at least one hemodynamic parameter of d) represents at least one hemodynamic index of a coronary vessel surrounding the myocardium.

13. The method of claim 12, wherein:
the at least one hemodynamic index relates to fractional flow reserve, coronary flow reserve, instantaneous wave-free ratio, hyperemic myocardium perfusion, index of microcirculatory resistance or other hemodynamic parameter along a coronary vessel surrounding the myocardium.

14. The method of claim 1, wherein:
the feature vectors of f) represent variation in a characteristic of interest over voxels within clusters of myocardial voxels; and/or
the feature vectors of f) are derived by calculating variation factors for the data encodings; and/or
the variation factor for a given data encoding represents a deviation of a characteristic of interest over all clusters for the given data encoding; and/or
the feature vectors of f) are derived from factors representing a characteristic of interest over multiple segments of the myocardium of the heart; and/or
the characteristic of interest represents a mean intensity computed by a multidimensional gaussian operator; and/or
the feature vectors of f) include additional information selected from the group consisting of: i) information that characterizes global features of the entire myocardium of the heart, ii) patient demographic information, iii) information that characterizes the presence or amount or type of coronary artery calcification or plaque, iv) information characterizing tissue composition or tissue type or contrast agent, v) information characterizing myocardium layering or myocardium layer, vi) information characterizing an ECG signal parameter, vii) information pertaining to a cardiac biomarker in blood such as cardiac troponin or creatine kinase, viii) information that characterizes fat surrounding the heart or inside the heart, ix) information that characterizes shape of the myocardium, x) information that characterizes myocardial strain, xi) information that characterizes blood volume or blood pressure, xii) information that characterizes ejection fraction, xiii) information that characterizes cardiac output, and xiv) information that characterizes parts of the heart, ascending aortic or coronary tree.

15. The method of claim 1, wherein:
the operations of a) to h) are performed by at least one processor.

16. A system for assessing vessel obstruction, comprising:
memory configured to store a contrast enhanced volume image dataset for a heart; and
one or more processors that, when executing program instructions stored in the memory, are configured to perform the method of claim 1.

* * * * *